(12) United States Patent
Barkeloo et al.

(10) Patent No.: US 8,354,267 B2
(45) Date of Patent: Jan. 15, 2013

(54) MICROBIAL FUEL CELL

(75) Inventors: Jason E. Barkeloo, Cincinnati, OH (US); Daniel J. Hassett, Cincinnati, OH (US); Randall T. Irvin, Sherwood Park (CA)

(73) Assignees: Bacterial Robotics, LLC, Cincinnati, OH (US); University of Cincinnati, Cincinnati, OH (US)

( * ) Notice: Subject to any disclaimer, the term of this patent is extended or adjusted under 35 U.S.C. 154(b) by 183 days.

(21) Appl. No.: 12/660,200

(22) Filed: Feb. 23, 2010

(65) Prior Publication Data
US 2010/0297737 A1 Nov. 25, 2010

Related U.S. Application Data

(60) Provisional application No. 61/154,464, filed on Feb. 23, 2009.

(51) Int. Cl.
*C12N 1/20* (2006.01)
(52) U.S. Cl. ................................. 435/252.34
(58) Field of Classification Search .................. None
See application file for complete search history.

(56) References Cited

U.S. PATENT DOCUMENTS

| 2008/0286624 A1 | 11/2008 | Lovley et al. |
| 2009/0324996 A1 | 12/2009 | Swift et al. |
| 2010/0297737 A1 | 11/2010 | Barkeloo et al. |

FOREIGN PATENT DOCUMENTS
WO PCT/US2010/055470 10/2011

OTHER PUBLICATIONS

Barkeloo, et al, An Extensible Microbial Fuel Cell System, Pilus Energy, LLC, Abstract #22, Nov. 17, 2009, Cincinnati, OH, U.S.A.
Bollinger,et al, "Gene Expression in Pseudomonas aeruginosa: Evidence of Iron Override Effects on Quorom Sensing and Biofilm-Specific Gene Regulation", J. Bacteriology, Mar. 2001, p. 1990-1996, v183:6.
Clean Energy Patent Growth Index, Cleantech Group, Heslin Rothenberg Farley and Mesiti PC, Nov. 10, 2009.
Genbank Accession No. NC_002516, Pseudomonas aeruginosa PAO1, complete genome, GI 110645304, 2000.
NirS Genbank Accession No. NC_011770.1, Pseudomonas aeruginosa LESB58 complete genome, GI 218888746, 2008.
Hoang et al, "A broad-host-range Flp-FRT recombination system for site-specific excision of chromosomally-located DNA sequences: application for isolation of unmarked Pseudomonas aeruginosa mutants", Gene, 1998, 77-86, v212, Elsevier.
Lovley, "Bug Juice: harvesting electricity with microorganisms", Nature Reviews Microbiology, Jul. 2006, p. 497-508, v4.
St John, Jeff, Clean Energy Patents Hit All-Time High in 4Q08, GreenTech Media, Feb. 13, 2009.
Logan, "Exoelectrogenic bacteria that power microbial fuel cells", Nature Reviews Microbiology, May 2009, p. 379-381, v.7.
Lovley, "Cleaning up with Genomics applying Molecular Biology to Bioremediation", Nature Reviews Microbiology, Oct. 2003, p. 35-44, v.1.
"It's electrifying", Nature Research Highlights:Bioelectronics, Aug. 20, 2009, p. 934, v.460.
Heydorn et al, "Statistical Analysis of Pseudomonas aeruginosa Biofilm Development: Impact of Mutations in Genes Involved in Twitching Motility, Cell to Cell Signaling, and Stationary-Phase Sigma Factor Expression", Applied & Environmental Microbiology, Apr. 2002, p. 2008-2017, v. 68:4.
Jalbuena et al, "Scientists turn to microbes to produce hydrogen fuel", Ecoseed, Jun. 7, 2010.
FtsZ, Genbank Acc. No. NC_002516, Pseudomonas aeruginosa GI:110645304, 2000.
Lasl, Genbank Acc. No. NC_002516, Pseudomonas aeruginosa GI:110645304, 2000.
PilA, Genbank Acc. No. NC_002516, Pseudomonas aeruginosa GI:110645304, 2000.
PilT, Genbank Acc. No. NC_002516, Pseudomonas aeruginosa GI:110645304, 2000.
BdlA, Genbank Acc. No. NC_002516, Pseudomonas aeruginosa GI:110645304, 2000.
FliC, Genbank Acc. No. NC_002516, Pseudomonas aeruginosa GI:110645304, 2000.
LasR, Genbank Acc. No. NC_002516, Pseudothonas aeruginosa GI:110645304, 2000.
Chiang et al, Biofilm formation by hyperpiliated mutants of Pseudomonas aeruginosa, Journal of Bacteriology, vol. 185(7), pp. 2374-2378 (Apr. 2003).
Ching et al, Genome-wide analysis of the RpoN regulon in Geobacter sulfurreducens, BMC Genomics, vol. 10:331 (Jul. 22, 2009).
Tandukar et al, Biological chromium (VI) reduction in the cathode of a microbial fuel cell, Environmental Science and Technology, vol. 43(21), pp. 8159-8165 (Nov. 1, 2009).
Herrell, Keith, Bacterium May Provide Alternative Power Source in Microbial Fuel Cells, UC HealthNews, UC Academic Health Center Public Relations & Communications, University of Cincinnati, Cincinnati, Ohio, Dec. 2010 [http://www.healthnews.uc.edu/publications/findings/?/12086/12094].
Wesoff, Eric, Energy Storage: McPhy's Hope for Hydrogen, greentechmedia, Jul. 6, 2010 [http://www.greentechmedia.com/articles/read/hope-for-the-hydrogen-economy].

*Primary Examiner* — Gary B. Nickol
*Assistant Examiner* — Khatol Shahnan-Shah
(74) *Attorney, Agent, or Firm* — Nevrivy Patent Law Group P.L.L.C.

(57) ABSTRACT

Transgenic microbes with an altered electrogenic efficacy, biofilms comprising such microbes, and microbial fuel cells comprising such microbes are provided. The microbial fuel cells can be operated as monitors, filtration devices, and sensors.

14 Claims, 7 Drawing Sheets

MICROBIAL FUEL CELL

CROSS-REFERENCE TO RELATED APPLICATIONS

This application claims priority to, and the benefit of U.S. Provisional Patent Application No. 61/154,464 filed on Feb. 23, 2009 which is incorporated herein by reference in its entirety.

This application may be related to co-pending U.S. patent application Ser. No. 12/660,244, entitled "IMPROVED MICROBIAL FUEL CELL," filed Feb. 23, 2010, by Barkeloo et al., the entire disclosure of which is incorporated herein by reference in its entirety.

FIELD OF THE INVENTION

The present application relates generally to genetically modified organisms, particularly genetically modified bacteria having an improved function in microbial fuel cells, more particularly to genetically modified bacteria with improved power (electron) generation, improved electron transfer, improved contact with the anode, and/or improved biofilm formation.

BACKGROUND OF THE INVENTION

Some bacteria can gain energy by transferring electrons from a low-potential substrate such as for example, glucose, to a high-potential electron acceptor such as for example, molecular oxygen ($O_2$) in a process commonly referred to as respiration. In eukaryotic cells, mitochondria obtain energy in the form of ATP through the processes of oxidation and phosphorylation, commonly referred to as oxidative phosphorylation. Gram-negative bacteria such as *Pseudomonas aeruginosa* function similarly to the eukaryotic mitochondria in producing energy. *P. aeruginosa* is a Gram-negative, rod-shaped bacterium with a single polar flagellum. An opportunistic human pathogen, *P. aeruginosa* is also an opportunistic pathogen of plants. *P. aeruginosa* is capable of growth at ranges of 4° C. to 42° C. It can live in diesel fuel and jet fuel where it is a hydrocarbon utilizing microorganism. It can also metabolize high nitrate-containing organic materials. *P. aeruginosa* derive electrons from a myriad of carbon sources and can derive electrons in aerobic, anaerobic and anaerobic fermentative processes (e.g., with arginine or pyruvate). In anaerobic growth, *P. aeruginosa* cells continue to couple oxidation and phosphorylation to gain energy.

In forms of microbial fuel cells, a microbe donates electrons to an anode rather than the natural recipient molecule such as oxygen, nitrate, or sulfate. Various types of microbes including bacteria and fungi have been demonstrated to generate electrical energy during metabolism, but microbial fuel cells most commonly utilize bacteria such as *Geobacter* or *Shewanella*. *Geobacter* cells respond to high microbial density in such a way as to interfere with large surface area biofilm formation.

In forms of microbial fuel cells, metabolic processes in the microbe generate energy in the form of electrons, especially in the anaerobic biofilm mode of growth. Rather than utilizing the energy, in a microbial fuel cell the microbe donates the electrons from a myriad of metabolized substrates to the anode for transfer through an electrical circuit. The electrical circuit carries electricity through a load, which represents work to be performed by the electron flow. The load may be a light emitting device, machinery, LCD, electrical appliance, battery charger, and many other devices.

Generally, microbes such as bacteria utilize a coenzyme known as nicotinamide adenine dinucleotide or $NAD^+$ to accept electrons from, and thus oxidize, a feedstock or substrate. The $NAD^+$ cleaves two hydrogen atoms from a reactant substrate. The $NAD^+$ accepts one of the hydrogen atoms to become NADH and gains an electron in the process. A hydride ion, or cation, is released. The equation is as shown below, where $RH_2$ is oxidized, thereby reducing $NAD^+$ to NADH. $RH_2$ could represent an organic substrate such as glucose or other organic matter such as organic waste.

$$RH_2 + NAD^+ \rightarrow NADH + H^+ + R \qquad \text{Eq. 1}$$

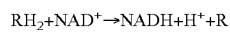

NADH is a strong reducing agent that the bacteria use to donate electrons when reducing another substrate. NADH reduces the other substrate and is concurrently reoxidized into $NAD^+$. In the natural state, the other substance may be oxygen or sulphate. In a microbial fuel cell the other substance may be a mediator or an anode. A mediator transfers electrons to the anode. The electrons, prevented from moving directly from the anode to the cathode, transfer to the cathode through an external electrical circuit and through the load perform useful work.

SUMMARY OF THE INVENTION

The application provides transgenic microbial cells stably transformed with an isolated nucleic acid molecule wherein the microbial cell exhibits altered expression of a nucleotide sequence (gene) of interest and an altered electrogenic efficacy. In aspects of these microbial cells, the isolated nucleic acid molecule comprises an expression cassette comprising a promoter operably linked to a heterologous nucleotide sequence of interest. The cell may exhibit altered expression of the heterologous nucleotide sequence of interest such as expression of a new or different polypeptide in the cell. Expression of the heterologous nucleotide side of interest may be increased in the transgenic (mutant) cell as compared to expression of the nucleotide sequence of interest in a non-transgenic cell (often referred to as wild-type). In an aspect, the promoter is selected from the group comprising inducible promoters and constitutive promoters. The transgenic microbial cell may further comprise a second expression cassette. In aspects of the invention the first expression cassette may comprise a second heterologous nucleotide sequence of interest.

In an embodiment, the isolated nucleic acid molecule disrupts an endogenous nucleotide sequence of interest. In aspects of the embodiment, a fragment of the isolated nucleic acid molecule is removed from the cell and the cell stably maintains the disrupted endogenous nucleotide sequence of interest. In an aspect, the microbial cell exhibits decreased expression of the endogenous nucleotide sequence of interest.

In an embodiment, the microbial cell is selected from the group comprising bacterial cells and fungal cells. A bacterial cell may be selected from the group of electron transferring bacteria including but not limited to *Pseudomonas*, *Geobacter*, *Shewanella*, and *Rhodoferax*, particularly *Pseudomonas aeruginosa* and *Pseudomonas putida*.

In an embodiment a transgenic bacterial cell selected from the group of electron transferring bacteria comprises a disrupted endogenous nucleotide sequence of interest. The disrupted endogenous nucleotide sequence of interest is selected from the group comprising pilT (SEQ ID NO:1), pilA (SEQ ID NO:2), nirS (SEQ ID NO:3), bdlA (SEQ ID NO:4), lasI (SEQ ID NO:5), lasR (SEQ ID NO:6), ftsZ (SEQ ID NO:7), and fliC (SEQ ID NO:8). In an aspect, the transgenic bacterial cell comprises at least two disrupted endogenous nucleotide sequence of interest selected from the group comprising pilT (SEQ ID NO:1), pilA (SEQ ID NO:2), nirS (SEQ ID NO:3), bdlA (SEQ ID NO:4), lasI (SEQ ID NO:5), lasR (SEQ ID NO:6), ftsZ (SEQ ID NO:7), and fliC (SEQ ID NO:8). In various aspects, the transgenic bacterial cell comprises at least three, at least four, at least five, at least six, at least seven, or at least eight disrupted endogenous nucleotide sequences of interest selected from the group comprising pilT (SEQ ID NO:1), pilA (SEQ ID NO:2), nirS (SEQ ID NO:3), bdlA (SEQ ID NO:4), lasI (SEQ ID NO:5), lasR (SEQ ID NO:6), ftsZ (SEQ ID NO:7), and fliC (SEQ ID NO:8).

In an aspect, the transgenic bacterial cell has a reduced proliferative capability as compared to a non-transgenic cell. In an aspect, the transgenic bacterial cell has a reduced virulence as compared to a non-transgenic cell. The reduced virulence may be in mammals or plants. In an aspect the transgenic bacteria cell exhibits reduced motility as compared to a non-transgenic cell. In an aspect the transgenic bacterial cell exhibits altered pilus sticking as compared to a non-transgenic cell. In an aspect the transgenic bacterial cell exhibits altered twitching motility as compared to a non-transgenic cell. In an aspect the transgenic bacterial cell has an altered iron-containing cytochrome concentration, particularly the iron-containing cytochrome concentration at or near the cytoplasmic membrane of the cell. In an aspect the transgenic bacterial cell has an altered concentration of a channel forming protein, particularly the channel forming concentration of the outer membrane of the cell. In an aspect the transgenic bacterial cell exhibits an increased current output/bacterial cell when the bacterial cell is a component of a microbial fuel cell. In an aspect the transgenic bacteria exhibits increased electron transfer to an anode, directly or indirectly.

In an embodiment the application provides a matrix comprising a transgenic bacterial cell selected from the group of electron transferring bacteria and exhibiting an altered electrogenic efficacy. In an aspect the matrix is selected from the group comprising sponges, filters, beads, powders, tissues, cassettes, cartridges and capsules.

In an embodiment the application provides a biofilm comprising a transgenic bacterial cell selected from the group of electron transferring bacteria and exhibiting an altered electrogenic efficacy. Biofilm thickness ranges between 1 µm to 300 µm, 10 µm to 200 µm, 10 µm to 30 µm, and 30 µm to 100 µm.

A filtration device comprising a transgenic bacterial cell selected from the group of electron transferring bacteria and exhibiting an altered electrogenic efficacy is provided. A filtration device may comprise a biofilm comprising a transgenic bacterial cell. The filtration device may further comprise an indicator. The filtration device may be a liquid material filtration device or a gaseous material filtration device. In aspect of a gaseous material filter, the transgenic bacteria utilize a greenhouse gas as a feedstock. The greenhouse gas may be selected from the group comprising carbon dioxide, $NO_2$, $NO_3$, $SO_2$, methane, $N_2O$, and $SO_3$.

An embodiment provides a microbial fuel cell comprising a transgenic bacterial cell selected from the group of electron transferring bacteria and exhibiting an altered electrogenic efficacy, an anode chamber and a cathode chamber. In an aspect, the transgenic bacterial cell is *Pseudomonas aeruginosa* or *Pseudomonas putida*. In an aspect, the anode chamber is detachable. In an aspect, the microbial fuel cell comprises a biofilm comprising a transgenic bacterial cell selected from the group of electron transferring bacteria and exhibiting an altered electrogenic efficacy. In an aspect the biofilm is attached to either the anode or the cathode. In an aspect, the biofilm is exposed to a feedstock. The feedstock may be selected from the group comprising sewage, fertilizer run-off, industrial wastes (e.g., dairy, canning, brewery, distillery, juice), rendering wastes, institutional wastes (schools, hospitals, nursing homes, prisons), military, landfill leachates and animal wastes. In an aspect, the feedstock is a gaseous material, perhaps comprising a greenhouse gas. In an aspect the feedstock is circulated; in an aspect the feedstock is bubbled; in an aspect the feedstock is static. In an embodiment the feedstock can be replaced. In an embodiment, anaerobic conditions are maintained around the biofilm in the anodic chamber. In an aspect, the anodic chamber may be pretreated with a biofilm inhibitor such as a polypeptide or small peptide.

In an embodiment the microbial fuel cell further comprises a mediator. The mediator may be an exogenous mediator or a pilus. The mediator may be selected from the group comprising thionine, methyl viologen, methylene blue, humic acids, neutral red, pyocyanin, pyorubrin, pyomelanin, 1-hydroxyphenazine and homogentisate. In an aspect, the mediator exhibits bacteriocidal or bacteriostatic activity.

The application provides a sensor for detecting at least one predetermined compound comprising a microbial fuel cell comprising a transgenic bacterial cell and an indicator. The indicator may be visual or audible. The indicator may indicate an abnormal level of the predetermined compound. The sensor may further comprise a second transgenic bacterial cell for detecting a second predetermined compound.

In an embodiment, the microbial fuel cell further comprises an ultracapacitor. In an aspect, the microbial fuel cell further comprises a water transfer component. In various aspect, the water transfer component transfers water produced by the microbial fuel cell to a water collection device or the external environment. In an aspect the microbial fuel cell further comprises a hydrogen transfer component and may further comprise a hydrogen fuel cell.

A bio-remedial system comprising a microbial fuel cell comprising a transgenic bacterium with altered electrogenic efficacy is provided. The transgenic cell of the bio-remedial system utilizes a predetermined compound as a feedstock. The predetermined compound may be selected from the group comprising methane, a greenhouse gas and uranium. In an aspect of the system, the transgenic bacterial cell converts the predetermined compound into a second compound.

The application provides an electrogenic efficacy cassette. The electrogenic efficacy cassette is an isolated nucleic acid molecule comprising an expression cassette comprising a promoter operably linked to a first nucleotide sequence of interest wherein the first nucleotide sequence of interest encodes a polypeptide that alters electrogenic efficacy. The isolated nucleic acid molecule may further comprise a second nucleotide sequence of interest wherein the second nucleotide sequence of interest also encodes a polypeptide that alters electrogenic efficacy.

Figure 1A:
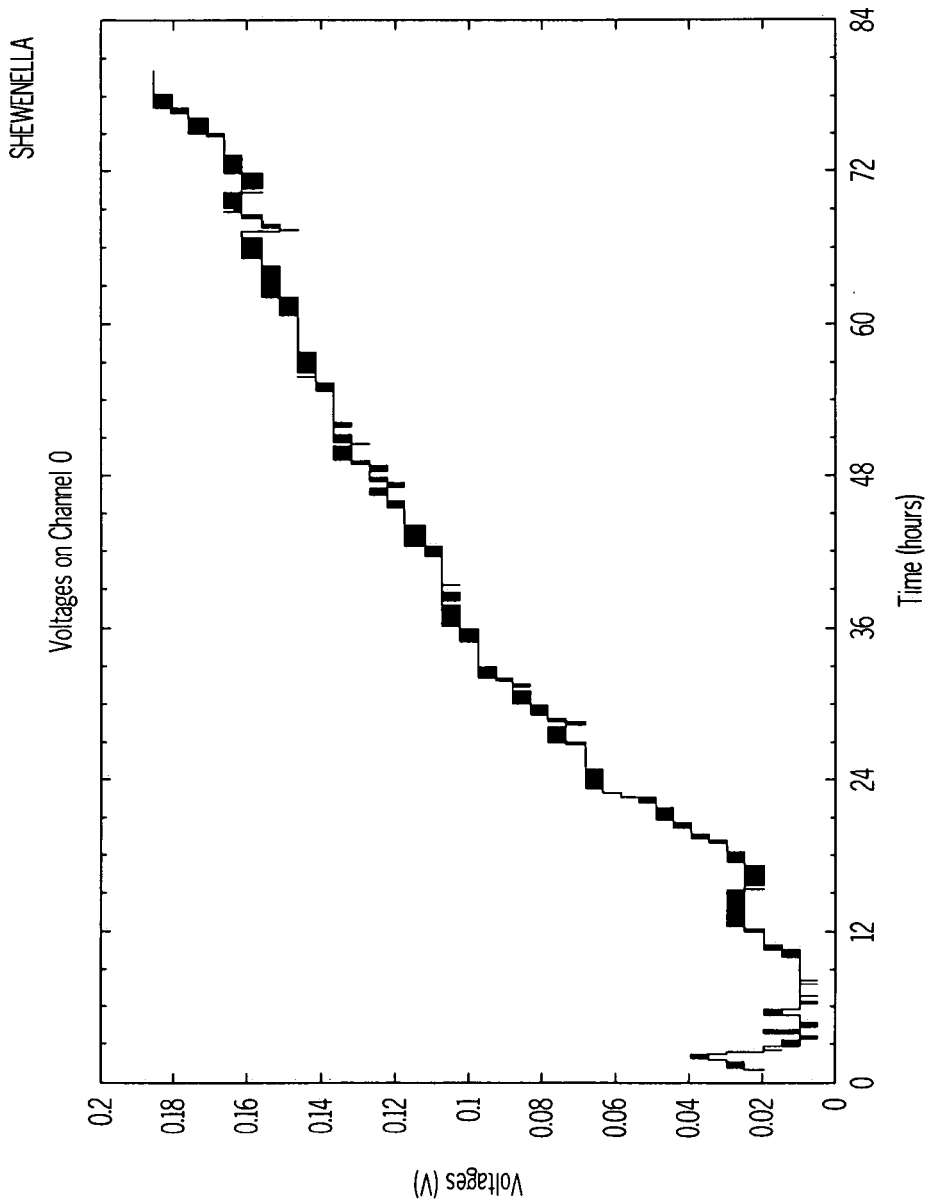
FIG. 1 presents electrogenic test data from experiments utilizing a 2.5 cm diameter anode. The panels present voltages measured on four different channels corresponding to microbial fuel cells comprising different microbes. In all the panels voltage is indicated on the y axis in volts. Time progression is indicated on the x axis; the microbial fuel cells were monitored for 3.5 days. Panel A presents voltages obtained from *Shewenella*; the voltage increases throughout the monitoring period, reaching almost 0.2 V. Panel B (channel 1) presents voltages obtained from a transgenic *P. aerugi-* nosa; the voltage fluctuates throughout the monitoring period with an early peak between 0.2 and 0.22 V. Panel C (channel 2) presents voltages obtained from a second transgenic *P. aeruginosa*; the voltage is high (0.3 V) early in the monitoring period and rapidly drops. Panel D (channel 3) presents voltages obtained from a third transgenic *P. aeruginosa*; the voltage fluctuates between 0.005 V and 0.05 V. Panel E (channel 4) presents voltages obtained from a fourth transgenic *P. aeruginosa*, a pilT mutant; the voltage starts near 0.5 V then decreases as the feedstock is consumed. The results from the fourth transgenic *P. aeruginosa* indicate that the voltage produced exceeds the voltage produced in the microbial fuel cell containing *Shewanella*.
Figure 1B:
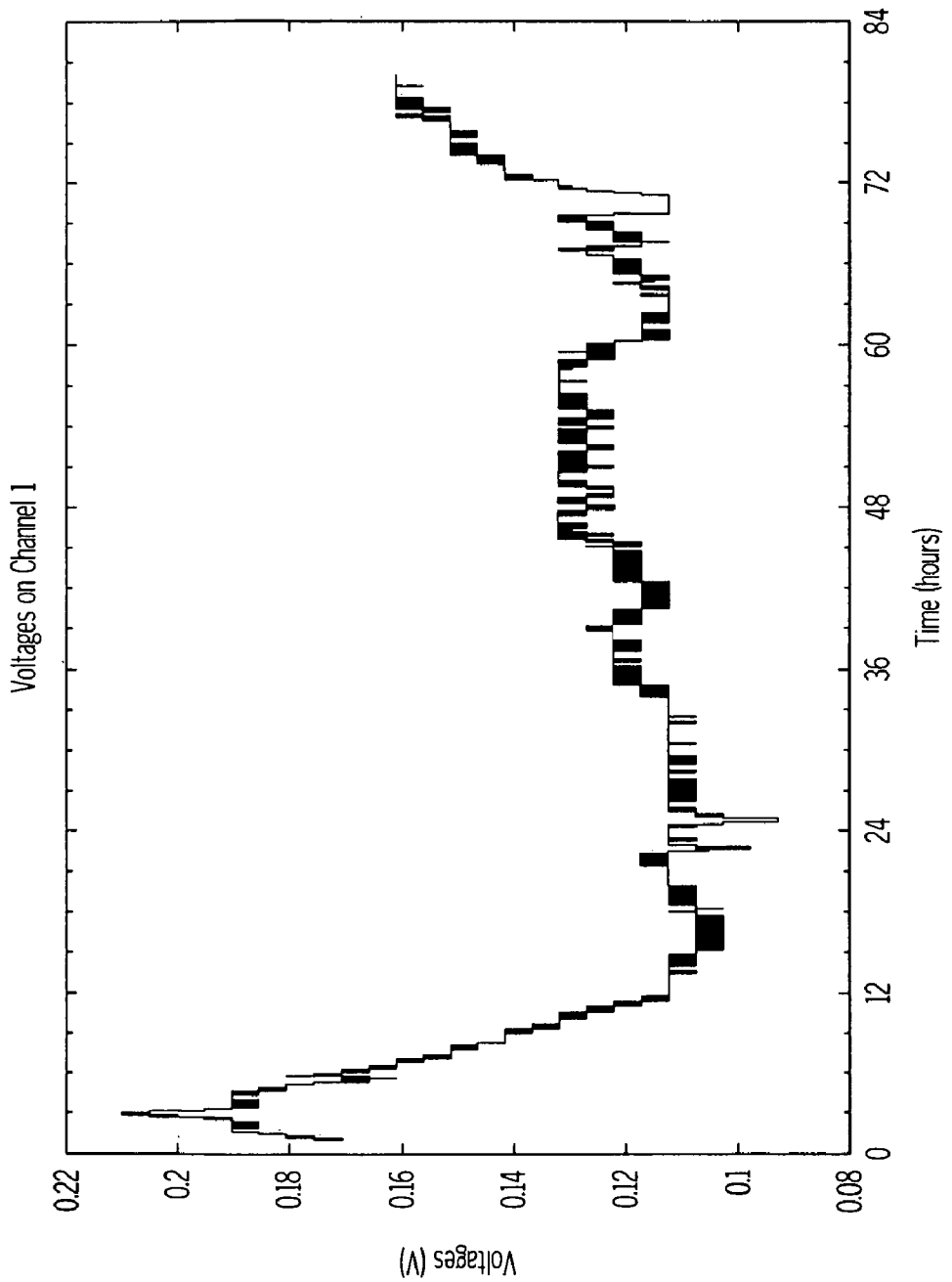
Figure 1C:
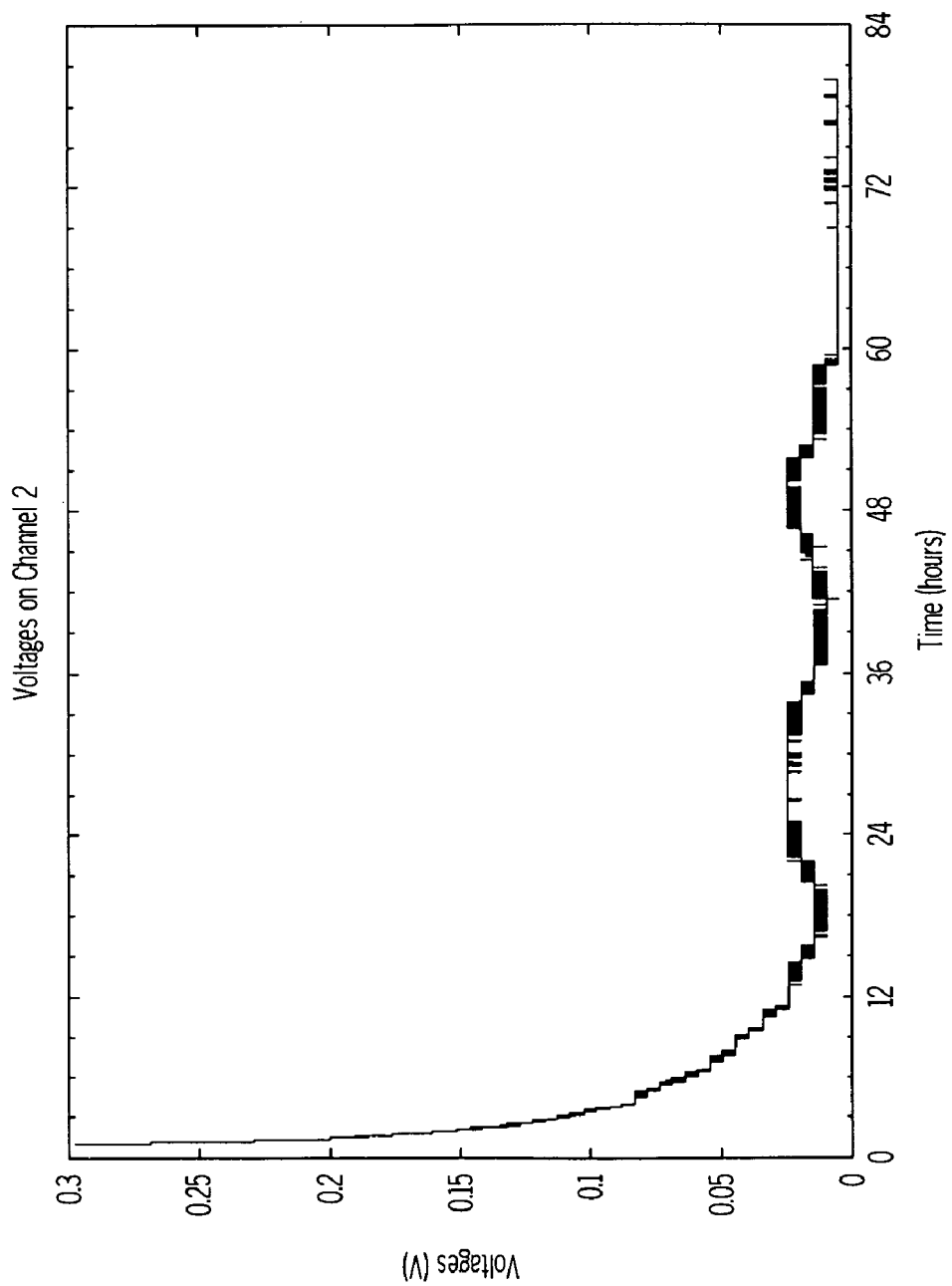
Figure 1D:
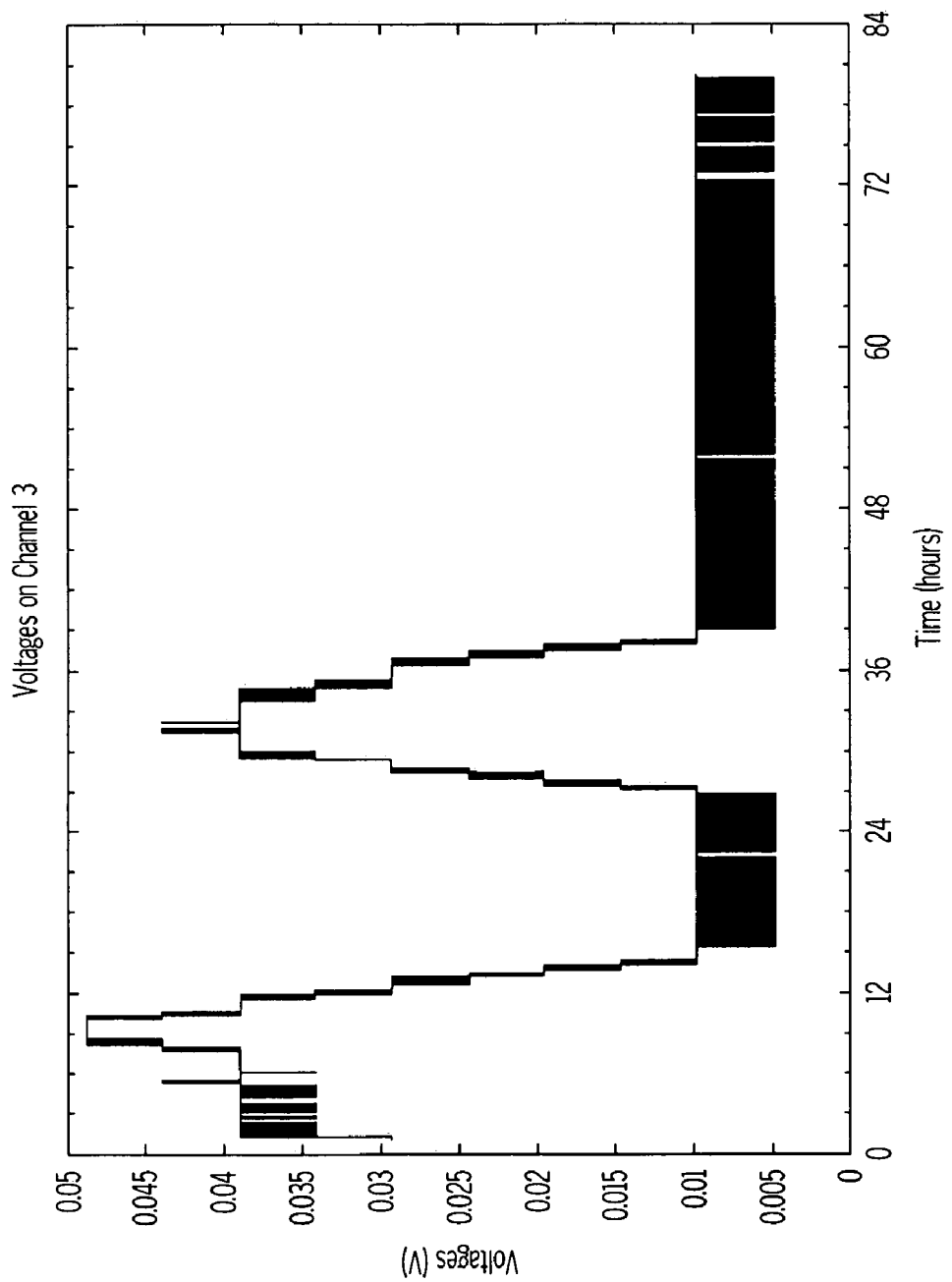
Figure 1E:
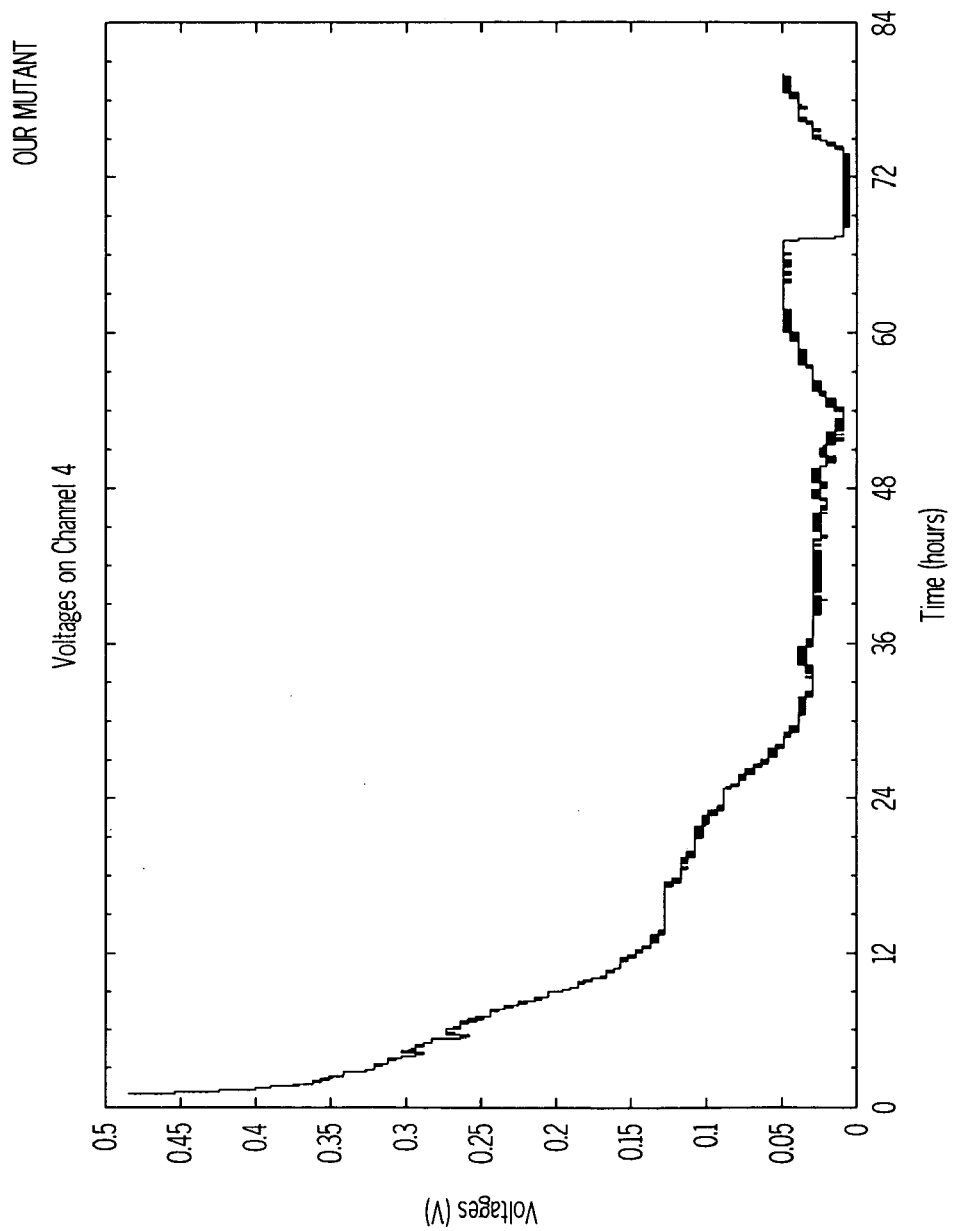
Figure 2:
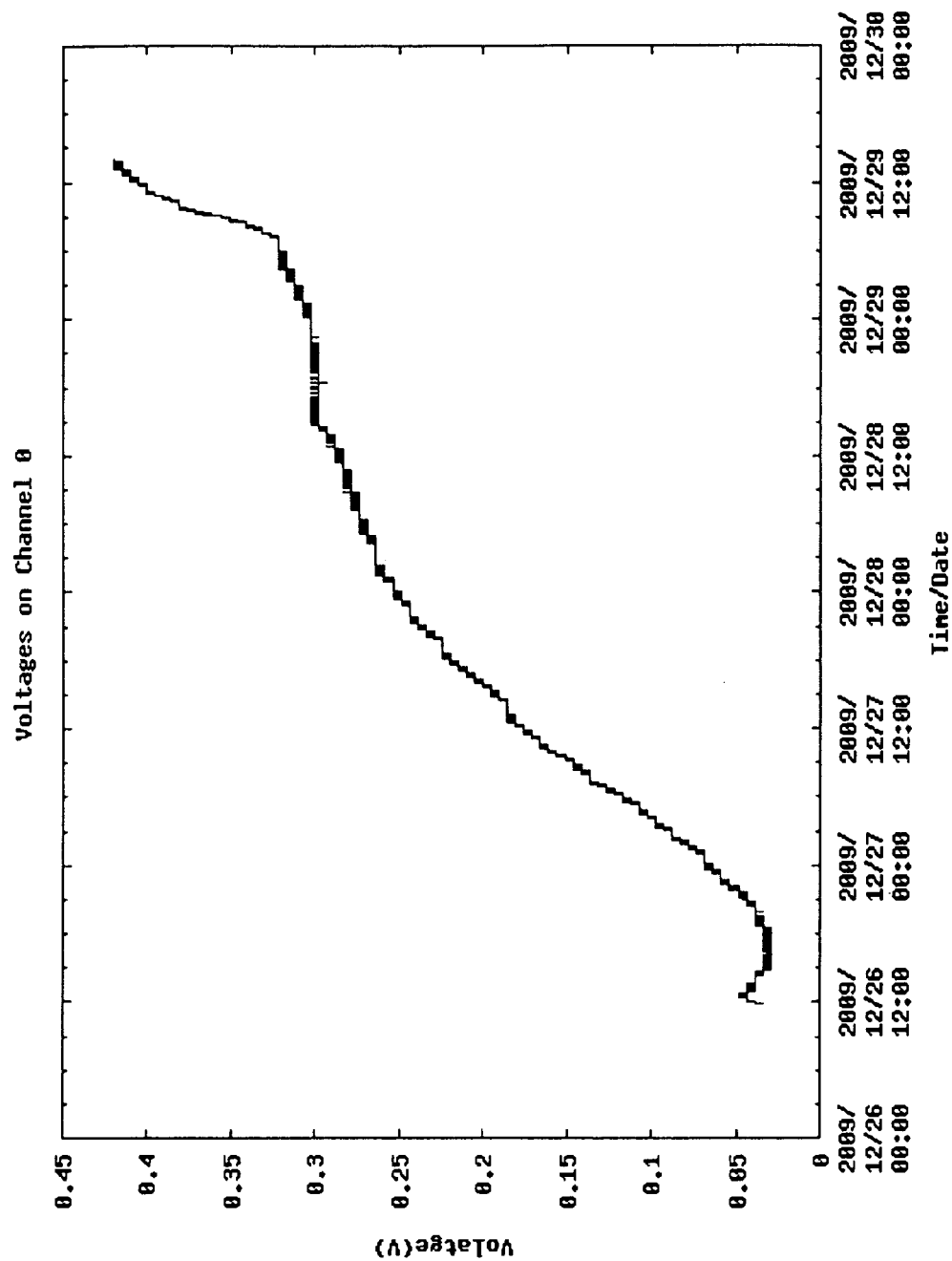

FIG. 2 presents voltages obtained from transgenic *P. aeruginosa*, a pilT mutant; the voltage starts below 0.05 V and rises to nearly 0.45 V. These voltometric measurements are from a single 13 ml fuel cell.

Figure 3:
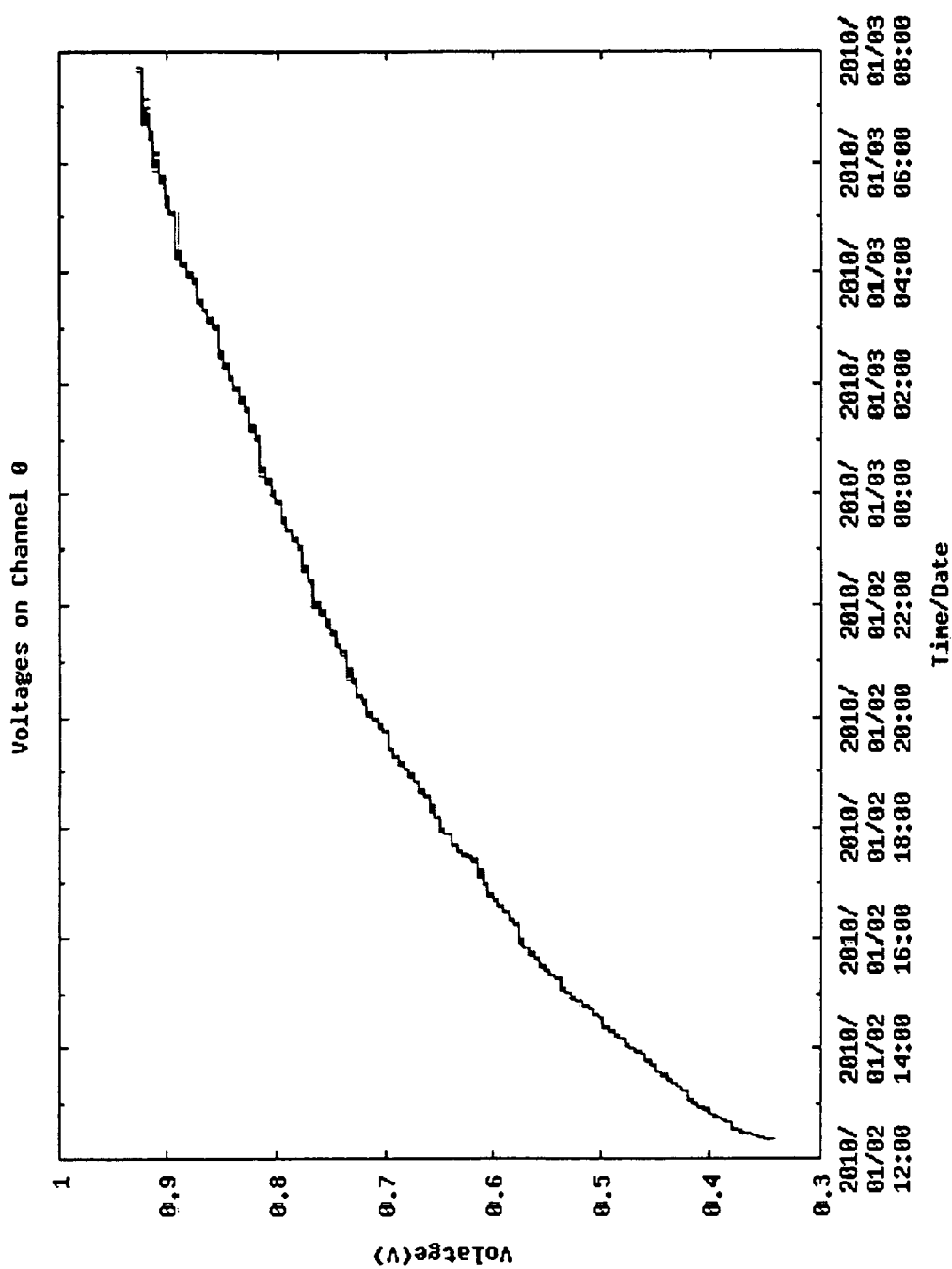

FIG. 3 presents voltages obtained from transgenic *P. aeruginosa*, a pilT mutant; the voltage starts between 0.3 and 0.4 V and rises to nearly 1 V. These voltometric measurements are from three 13 ml fuel cells connected in series.

DETAILED DESCRIPTION OF THE INVENTION

Microbial cells that can generate electrical current from a metabolite include, but are not limited to bacteria and fungi. Bacterial cells that can transfer electrical current to an external component include, but are not limited to *Synechocystis* sp PCC 6803, *Brevibacillus* sp. PTH1, *Pseudomonas* sp., *Psuedomonas aeruginosa* (*P. aeruginosa*), *Pseudomonas putida*, *Shewanella* sp, *Shewanella oneidensis* MR-1, *Shewanell putrefaciens* IR-1, *Shewanella oneidensis* DSP10, *Geobacter* sp., *Geobacter sulfurreducens*, *Geobacter metalireducens*, *Peletomaculum thermopropionicum*, *Methanothermobacter thermautotrophicus*, *Ochrobactrum anthropi*, *Clostridium butyricum* EG3, *Desulfuromonas acetoxidans*, *Rhodoferax ferrireducens*, *Aeromonas hydrophila*. A3, *Desulfobulbus propionicus*, *Geopsychrobacter electrodiphilus*, *Geothrix fermentans*, *Escherichia coli*, *Rhodopseudomonas palustris*, *Ochrobactrum anthropi* YZ-1, *Desulfovibrio desulfuricans*, *Acidiphilium* sp.3.2Sup5, *Klebsiella pneumonia* L17. Fungal cells that can generate electrical current from a metabolite include, but are not limited to *Pichia anomala*. See for example, Prasad et al. (2007) *Biosens. Bioelectron.* 22:2604-2610; Gorby et al. (2006) *Proc. Natl. Acad. Sci. USA* 103:11358-11363; Pham et al (2008) *Appl. Microbiol. Biotechnol.* 77:1119-1129; and El-Nagger et al (2008) *Biophys J.* 95:L10-L12; herein incorporated by reference in their entirety. Microbial cells that are capable of exocellular electron transfer are sometimes described as "exoelectrogens", "electrochemically active microbes", "electricigens", "anode respiring microbes", "electrochemically active bacteria", and "anode respiring bacteria".

By "electrogenic efficacy" is intended the capability to transfer electrons to or from an anode or a cathode. Such a transfer may be direct or indirect via a mediator. With regard to the electrogenic efficacy of a microbial cell, numerous components or characteristics of the cell impact electrogenic efficacy. A component or characteristic that impacts electrogenic efficacy is an electrogenic component or electrogenic characteristic. Such electrogenic-related characteristics include, but are not limited to, biofilm related characteristics such as biofilm forming abilities, biofilm density, tolerance for existence in a biofilm, cell packing characteristics, quorum sensing characteristic, cell growth rate, cell division rate, cell motility, substrate attachment, substrate adhesion, enzymatic processing of a feedstock, oxidation, phosphorylation, reduction, electron transfer, twitching motility, piliation, cell to cell adhesion, nanowire formation, nanowire structure, the ability to disperse from the biofilm and mediator related characteristics. Electrogenic efficacy can be measured using volt or current Measuring devices known in the art (multimeters and computer-based measuring techniques).

Microbes may obtain energy from a feedstock or material through a metabolic process. In a microbial fuel cell, the transgenic microbes have access to a feedstock. In an embodiment the feedstock is in the anodic chamber. In an embodiment the feedstock is circulated past the anode. In an aspect it is recognized that the feedstock and/or the transgenic microbes are replaced, removed, or reseeded. Greenhouse gases include, but are not limited to, carbon dioxide ($CO_2$), nitrous oxide ($N_2O$), methane, sulfur dioxide ($SO_2$), $NO_2$, $NO_3$, and $SO_3$.

*P. aeruginosa* metabolizes a variety of feedstocks to produce energy. *P. aeruginosa* may utilize high nitrate organic materials including, but not limited to, sewage, fertilizer runoff, pulping plant effluent, and animal waste; and hydrocarbons such as diesel fuel and jet fuel; greenhouse gases, and solutions or gaseous material with a high nitrate concentration.

*P. aeruginosa* attaches directly and tightly to metal substrates by means of surface-exposed proteinaceous appendages known as pili (also referred to as nanowires). The attached pili allow electron transfer from the bacteria to the insoluble substrate, in a fashion similar to nanowires. See Yu et al. (2007) *J. Bionanoscience* 1:73-83, herein incorporated by reference in its entirety. *P. aeruginosa* forms biofilms in a variety of conditions including both aerobic and anaerobic conditions; anaerobic conditions result in improved biofilm formation (Yoon et al., 2002. *Pseudomonas aeruginosa anaerobic respiration in biofilms: relationships to cystic fibrosis pathogenesis*. Dev. Cell. 3: 593-603). During anaerobic conditions, electrons are donated to the anode surface. The protons (H+) then can react at the cathodic surface to yield hydrogen gas as a byproduct. In aerobic conditions, *P. aeruginosa* yields water as a byproduct at the cathode in a microbial fuel cell or during planktonic (free-swimming) growth.

An electrogenic component may include any polypeptides, peptides, or compounds involved in electrogenesis including but not limited to transporters, ion transporters, pilus components, membrane components, cytochromes, quorum sensors, redox active proteins, electron transfer components, pyocyanin, pyorubrin, pyomelanin, 1-hydroxy-phenazine or homogentisate, uncoupler proteins (UCPs), and enzymes, pilin, pilT (SEQ ID NO:1), bdlA (SEQ ID NO:4), lasI (SEQ ID NO:5), lasR (SEQ ID NO:6), nirS (SEQ ID NO:3), ftsZ (SEQ ID NO:7), pilA (SEQ ID NO:2), and fliC (SEQ ID NO:8).

A transgenic microbe may exhibit an altered electrogenic efficacy. A transgenic microbial cell is a microbial cell stably transformed with an isolated nucleic acid molecule and that exhibits altered expression of a nucleotide sequence of interest. The isolated nucleic acid molecule may disrupt an endogenous nucleotide sequence of interest resulting in altered expression of the disrupted endogenous nucleotide sequence of interest or the isolated nucleic acid may comprise an expression cassette comprising a promoter operably linked to a heterologous nucleotide sequence of interest resulting in altered expression of the heterologous nucleotide sequence of interest. It is recognized that the transgenic microbes may contain multiple genetic alterations or mutations that inactivate the genes; these may include a one, two, three, four, five, six, seven, eight, nine, ten, eleven, twelve, thirteen, fourteen, fifteen, sixteen, seventeen, eighteen, nineteen, twenty or more stably incorporated mutations. Such a stably incorporated mutation may introduce a heterogenous nucleotide sequence of interest or disrupt an endogenous nucleotide sequence.

By "stably transformed" is intended that the genome of the microbe has incorporated at least one copy of the isolated nucleic acid molecule. When a stably transformed microbe divides, both daughter cells include a copy of the isolated nucleic acid molecule. It is envisioned that transgenic microbes include progeny of a stably transformed microbe. The invention encompasses isolated or substantially purified nucleic acid compositions. An "isolated" or substantially "purified" nucleic acid molecule, or biologically active portion thereof, is substantially free of other cellular material, or culture medium when produced by recombinant techniques or substantially free of chemical precursors or other chemicals when chemically synthesized. Isolated nucleic acid molecules may include vectors or plasmids purified from a host cell and fragments of a vector or plasmid purified from a host cell.

By "fragment" is intended a portion of an isolated nucleic acid molecule. Fragments of an isolated nucleic acid molecule may range from at least about 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950, 2000, 2050, 2100, 2150, 2200, 2250, 2300, 2350, 2400, 2450, 2500, 2550, 2600, 2650, 2700, 2750, 2800, 2850, 2900, 2950, 3000, 3050, 3100, 3150, 3200, 3250, 3300, 3350, 3400, 3450, 3500, 3550, 3600, 3650, 3700, 3750, 3800, 3850, 3900, 3950, 4000, 4050, 4100, 4150, 4200, 4250, 4300, 4350, 4400, 4450, 4500, 4550, 4600, 4650, 4700, 4750, 4800, 4850, 4900, 4950, 4500, 4550, 4600, 4650, 4700, 4750, 4800, 4850, 4900, 4950, 5000, 5050, 5100, 5150, 5200, 5250, 5300, 5350, 5400, 5450, 5500, 5550, 5600, 5650, 5700, or up to and including all the full number of nucleotides in an isolated nucleic acid molecule.

An isolated nucleic acid molecule may comprise a regulatable expression cassette. Expression cassettes will comprise a transcriptional initiation region comprising a promoter nucleotide sequences operably linked to a heterologous nucleotide sequence of interest whose expression is to be controlled by the promoter. Such an expression cassette is provided with at least one restriction site for insertion of the nucleotide sequence to be under the transcriptional regulation of the regulatory regions. The expression cassette may additionally contain selectable marker genes.

The expression cassette will include in the 5'-to-3' direction of transcription, a transcriptional and translational initiation region, and a heterologous nucleotide sequence of interest. In addition to containing sites for transcription initiation and control, expression cassettes can also contain sequences necessary for transcription termination and, in the transcribed region a ribosome-binding site for translation. Other regulatory control elements for expression include initiation and termination codons as well as polyadenylation signals. The person of ordinary skill in the art would be aware of the numerous regulatory sequences that are useful in expression vectors. Such regulatory sequences are described, for example, in Sambrook et al. (1989) *Molecular Cloning: A Laboratory Manual* 2nd. ed., Cold Spring Harbor Laboratory Press, Cold Spring Harbor, N.Y.).

The expression cassette comprising the promoter sequence operably linked to a heterologous nucleotide sequence may also contain at least one additional nucleotide sequence for a gene to be co-transformed into the organism. Alternatively, the additional sequence(s) can be provided on another expression cassette.

The regulatory sequences to which the polynucleotides described herein can be operably linked include promoters for directing mRNA transcription. These include, but are not limited to, the left promoter from bacteriophage A, the lac, TRP, and TAC promoters from *E. coli*, the early and late promoters from SV40, the CMV immediate early promoter, the adenovirus early and late promoters, and retrovirus long-terminal repeats.

In addition to control regions that promote transcription, expression vectors may also include regions that modulate transcription, such as repressor binding sites and enhancers. Examples include the SV40 enhancer, the cytomegalovirus immediate early enhancer, polyoma enhancer, adenovirus enhancers, and retrovirus LTR enhancers.

Where appropriate, the heterologous nucleotide sequence whose expression is to be under the control of the promoter sequence of the present invention and any additional nucleotide sequence(s) may be optimized for increased expression in the transformed microbe. That is, these nucleotide sequences can be synthesized using species preferred codons for improved expression. Methods are available in the art for synthesizing species-preferred nucleotide sequences. See, for example, Wada et al. (1992) *Nucleic Acids Res.* 20 (Suppl.), 2111-2118; Butkus et al. (1998) *Clin Exp Pharmacol Physiol Suppl.* 25:S28-33; and Sambrook et al. (1989) *Molecular Cloning: A Laboratory Manual* 2nd. ed., Cold Spring Harbor Laboratory Press, Cold Spring Harbor, N.Y., herein incorporated by reference.

Additional sequence modifications are known to enhance gene expression in a cellular host. The G-C content of the heterologous nucleotide sequence may be adjusted to levels average for a given cellular host, as calculated by reference to known genes expressed in the host cell. When possible, the sequence is modified to avoid predicted hairpin secondary mRNA structures.

The expression cassettes may additionally contain 5' leader sequences in the expression cassette construct. Such leader sequences can act to enhance translation. Translation leaders are known in the art and include: picornavirus leaders, for example, EMCV leader (Encephalomyocarditis 5' noncoding region) (Elroy-Stein et al. (1989) *Proc. Nat. Acad. Sci. USA* 86:6126-6130); potyvirus leaders, for example, TEV leader (Tobacco Etch Virus) (Allison et al. (1986)); MDMV leader (Maize Dwarf Mosaic Virus) (*Virology* 154:9-20); and human immunoglobulin heavy-chain binding protein (BiP) (Macejak et al. (1991) *Nature* 353:90-94). Other methods known to enhance translation and/or mRNA stability can also be utilized, for example, introns, and the like.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose; in vitro mutagenesis; primer repair; restriction; annealing; substitutions, for example, transitions and transversions; or any combination thereof may be involved.

Reporter genes or selectable marker genes may be included in the expression cassettes. Examples of suitable reporter genes known in the art can be found in, for example, Ausubel et al. (2002) *Current Protocols in Molecular Biology*. John Wiley & Sons, New York, N.Y., herein incorporated by reference.

Selectable marker genes for selection of transformed cells or tissues can include genes that confer antibiotic resistance. Examples of suitable selectable marker genes include, but are not limited to, genes encoding resistance to gemtamicin Schweizer, H. P. 1993. Small broad-host-range gentamicin resistance gene cassettes for site-specific insertion and deletion mutagenesis Biotechniques 15:831-833., carbenicillin Parvatiyar et al., 2005. Global analysis of cellular factors and responses involved in *Pseudomonas aeruginosa* resistance to arsenite. J Bacteriol 187:4853-64., chloramphenicol (Herrera Estrella et al. (1983) *EMBO J.* 2:987-992); methotrexate (Herrera Estrella et al. (1983) *Nature* 303:209-213; Meijer et al. (1991) *Plant Mol. Biol.* 16:807-820); hygromycin (Waldron et al. (1985) *Plant Mol. Biol.* 5:103-108; Zhijian et al. (1995) *Plant Science* 108:219-227); streptomycin (Jones et al. (1987) *Mol. Gen. Genet.* 210:86-91); spectinomycin (Bretagne-Sagnard et al. (1996) *Transgenic Res.* 5:131-137); bleomycin (Hille et al. (1990) *Plant Mol. Biol.* 7:171-176); sulfonamide (Guerineau et al. (1990) *Plant Mol. Biol.* 15:127-136); puromycin (Abbate et al (2001) *Biotechniques* 31:336-40; cytosine arabinoside (Eliopoulos et al. (2002) *Gene Ther.* 9:452-462); 6-thioguanine (Tucker et al. (1997) *Nucleic Acid Research* 25:3745-46).

Other genes that could serve utility in the recovery of transgenic events but might not be required in the final product would include, but are not limited to, examples such as levansucrase (sacB), GUS (β-glucoronidase; Jefferson (1987) *Plant Mol. Biol. Rep.* 5:387); GFP (green fluorescence protein; Wang et al. (2001) *Anim Biotechnol* 12:101-110; Chalfie et al. (1994) *Science* 263:802), BFP (blue fluorescence protein; Yang et al. (1998) *J. Biol. Chem.* 273:8212-6), CAT; and luciferase (Riggs et al. (1987) *Nucleic Acid Res.* 15 (19):8115; Luchrsen et al. (1992) *Methods Enzymol.* 216: 397-414).

A number of promoters can be used in the practice of the invention. The promoters can be selected based on the desired outcome. A variety of inducible promoter systems have been described in the literature and can be used in the present invention. These include, but are not limited to, tetracycline-regulatable systems (WO 94/29442, WO 96/40892, WO 96/01313, U.S. application Ser. No. 10/613,728); hormone responsive systems, interferon-inducible systems, metal-inducible systems, and heat-inducible systems, (WO 93/20218); ecdysone inducible systems, and araC-$P_{bad}$. Some of these systems, including ecdysone inducible and tetracycline inducible systems are commercially available from Invitrogen (Carlsbad, Calif.) and Clontech (Palo Alto, Calif.), respectively. See Qiu et al, (2008) *App. & Environ Microbiology* 74:7422-7426 and Guzman et al, (1995) *J. Bacteriol.* 177:4121-4130, herein incorporated by reference in their entirety.

By "inducible" is intended that a chemical stimulus alters expression of the operably linked nucleotide sequence of interest by at least 1%, 5%, preferably 10%, 20%, more preferably 30%, 40%, 50%, 60%, 70%, 80%, 90%, 99% or more. The difference may be an increase or decrease in expression levels. Methods for assaying expression levels are described elsewhere herein. The chemical stimulus may be administered or withdrawn. Various chemical stimuli are known in the art.

One of the most widely used inducible systems is the binary, tetracycline-based system, which has been used in both cells and animals to reversibly induce expression by the addition or removal of tetracycline or its analogues. (See Bujard (1999). *J. Gene Med.* 1:372-374; Furth, et al. (1994). *Proc. Natl. Acad. Sci. USA* 91:9302-9306; and Mansuy & Bujard (2000). *Curr. Opin. Neurobiol.* 10:593-596, herein incorporated by reference in their entirety.) Another example of such a binary system is the cre/loxP recombinase system of bacteriophage P1. For a description of the cre/loxP recombinase system, see, e.g., Lakso et al. (1992) *PNAS* 89:6232-6236. In the Cre/LoxP recombinase system, the activator transgene encodes recombinase. If a cre/loxP recombinase system is used to regulate expression of the transgene, microbes containing transgenes encoding both the Cre recombinase and a selected target protein are required. Another example of a recombinase system is the FLP recombinase system of *S. cerevisiae* (O'Gorman et al. (1991) *Science* 251:1351-1355. A single transgenic microbe may comprise multiple inducible promoters.

Methods of determining expression levels are known in the art and include, but are not limited to, qualitative Western blot analysis, immunoprecipitation, radiological assays, polypeptide purification, spectrophotometric analysis, Coomassie staining of acrylamide gels, ELISAs, RT-PCR, 2-D gel electrophoresis, microarray analysis, in situ hybridization, chemiluminescence, silver staining, enzymatic assays, ponceau S staining, multiplex RT-PCR, immunohistochemical assays, radioimmunoassay, colorimetric analysis, immunoradiometric assays, positron emission tomography, Northern blotting, fluorometric assays and SAGE. See, for example, Ausubel at al, eds. (2002) Current Protocols in Molecular Biology, Wiley-Interscience, New York, N.Y.; Coligan et al (2002) Current Protocols in Protein Science, Wiley-Interscience, New York, N.Y.; and Sun et al. (2001) *Gene Ther.* 8:1572-1579, herein incorporated by reference. It is recognized that expression of a nucleotide sequence of interest may be assessed, analyzed, or evaluated at the RNA, polypeptide, or peptide level.

By altered expression is intended a change in expression level of the full nucleotide sequence of interest as compared to an untransfomed, unmodified, non-transgenic, or wild-type microbe. Such a change may be an increase or decrease in expression. An expression level may increase approximately 1%, 2%, 3%, 4%, 5%, 10%, 20%, 30%, 40%, 50%, 60%, 70%, 80%, 90%, 100%, 200%, 300%, 400%, 500% or more. An expression level may decrease approximately 1%, 2%, 3%, 4%, 5%, 10%, 20%, 30%, 40%, 50%, 60%, 70%, 80%, 90%, or 100%. It is recognized that altered expression also includes expression of a fragment of the nucleotide sequence of interest rather than the full length nucleotide sequence of interest.

A transgenic cell may exhibit an altered cellular property such as, but not limited to, an altered electrogenic efficacy. Such an alteration may be an increase or decrease in the property of interest. It is recognized that an alteration in one cellular property may alter a second cellular property; it is further recognized that an increase in one property may decrease a second property, an increase in one property may increase a second property, a decrease in one property may decrease a second property, and a decrease in one property may increase a second property. An altered cellular property may be altered by 1%, 2%, 3%, 4%, 5%, 10%, 20%, 30%, 40%, 50%, 60%, 70%, 80%, 90%, 100%, 200%, 300%, 400%, 500% or more as compared to that cellular property in a non-transgenic microbial cell. Methods of analyzing cellular properties are known in the art.

An isolated nucleic acid molecule that disrupts an endogenous nucleotide sequence of interest may replace the endogenous nucleotide sequence of interest, may interrupt the endogenous nucleotide sequence, may replace a portion of the endogenous nucleotide sequence of interest, may replace a regulatory region controlling expression of the endogenous nucleotide sequence of interest, may interrupt the a regulatory region controlling expression of the endogenous nucleotide sequence, may delete an endogenous nucleotide sequence of interest, may delete a portion of an endogenous nucleotide sequence, may delete a regulatory region, or may delete a portion of a regulatory region. Endogenous nucleotide sequences of interest include, but are not limited to, pilT (SEQ ID NO:1), bdlA (SEQ ID NO:4), lasI (SEQ ID NO:5), lasR (SEQ ID NO:6), nirS (SEQ ID NO:3), ftsZ (SEQ ID NO:7), pilA (SEQ ID NO:2), and fliC (SEQ ID NO:8).

The pilT gene encodes a polypeptide involved in regulating the number of pili on the bacterial surface; the protein, an electrically conductive polypeptide, is also known as the twitching motility protein. Twitching motility is the movement of bacteria by extending the pili, attaching the pili to an inanimate or animate surface and retracting the pili. Certain pilT mutants, such as pilT disruptions, exhibit reduced twitching motility and increased piliation or hyperpiliation. These pilT mutants exhibit improved attachment, cell to cell adhesion, and biofilm formation. Certain pilT mutants exhibit decreased virulence and decreased ability to detach from surfaces. While not limited by mechanism, reduced twitching motility appears to increase attachment and cell to cell attachment thus improving biofilm formation and increasing biofilm thickness. See Chaing & Burrows (2003) *J. Bacterio.* 2374-2387, herein incorporated by reference in its entirety.

bdlA or biofilm dispersion locus A is involved in bacterial dispersion from biofilms. As it is desirable to maintain biofilms on anodic surfaces, altering the bacterial cells ability to perform chemotaxis may improve biofilm formation and maintenance. Chemotaxis is the process of bacterial movement toward or away from a variety of stimuli or repellents. Disruption or deletion of bdlA reduces the bacterial cell's ability to detach from a surface, thus improving biofilm formation and maintenance and increasing electron transfer to the anode. See Morgan et al (2006) *J. Bacteriol.* 7335-7343, herein incorporated by reference in its entirety.

The fliC gene encodes a polypeptide involved in swimming motility and chemotaxis. FliC disruption mutants do not have a flagellum; thus their motility is reduced. FliC disruption mutations exhibit reduced chemotaxis and improved biofilm formation. While not being limited by theory, FliC disruption mutants may transfer more electrons to an anode.

LasI encodes N-(3-oxododecanoyl)-L-homoserine lactone synthase, a polypeptide that, while not being limited by mechanism, may be involved in the process of cell to cell signaling known as quorum sensing. Certain N-(3-oxododecanoyl)-L-homoserine lactone synthase mutants have altered biofilm characteristics. These altered biofilm formation characteristics include, but are not limited to, thinner, more compact biofilms, increased cell density, altered surface attachment properties, altered polysaccharide production, decreased polysaccharide production, and altered production of pyocyanin. Pyocyanin is redox-active, exhibits antibiotic activity, and may function as a mediator of electron transfer. Deletion of lasI also alters virulence of the bacterial cell in both animal and human cells. Such an altered virulence may be a decreased virulence in a human or animal cell. See Davies et al (1998) *Science*, herein incorporated by reference in its entirety.

Deletion of lasR alters virulence of the bacterial cell in both animal and human cells. Such an altered virulence may be a decreased virulence in a human or animal cell. By virulence is intended the relative capacity of a pathogen to overcome a target's defenses. Microbial cells may infect any other living organism; a particular type of microbial cell may have a limited range of targets. *Pseudomonas aeruginosa* is capable of infecting a wide range of targets including plants, insects, mammals. Exemplary mammals include, but are not limited to humans, bovines, simians, ovines, caprines, swines, lapines, murines and camellids. Aspects of virulence include but are not limited to the scope of suitable targets, infectivity, multiplicity of infection, transfer speed from one target to another, target cell binding ability, antibiotic sensitivity, pathogenesis and antigen production. It is recognized that lowering one aspect of virulence may not impact another aspect of virulence or may increase another aspect of virulence.

NirS encodes respiratory nitrate reductase (NIR) precursor. Inactivated nirS mutants exhibit an altered ability to survive anaerobic culture in biofilms (Yoon et al (2002) *Dev Cell* 3:593, herein incorporated by reference in its entirety.). While not being limited by mechanism, NIR may be the second enzymatic step in the overall process of nitrate reduction to nitrogen gas during anaerobic respiration. The product of respiratory NIR is nitric oxide (NO), a compound that is inherently toxic to bacteria in micromolar concentrations. NIR may catalyze both the one electron reduction of $NO_2^-$ to NO and may catalyze the four-electron reduction of $O_2$ to $2H_2O$. Inactivation of nirS may reduce problems associated with NO in anaerobic biofilms, increase electron flow through the pili, and reduce production of nitrous oxide ($N_2O$). The surface-exposed Type III secretion apparatus of a nirS mutant generates lower toxin concentrations than wild-type bacteria; nirS mutants exhibit improved virulence properties. See Van Alst, N. E. et al., 2009. Nitrite reductase NirS is required for type III secretion system expression and virulence in the human monocyte cell line THP-1 by *Pseudomonas aeruginosa* Infect Immun 77: 4446-4454, herein incorporated by reference in its entirety.

By "biofilm" is intended a complex surface attached growth comprising multiple cells that are typically enmeshed or embedded within a polysaccharide/protein matrix. Biofilms occur in varying thickness; such thickness may change over time and may vary in different areas of the biofilm. Preferred thickness of a biofilm is within a range between 1 µm and 300 µm, particularly between 10 µm and 200 µm and more particularly between 30 and 100 µm. Biofilms may be comprised of multiple cell types, a single cell type, or a clonal population of cells. Multiple cell types may refer to cells of different species, cells of different strains of the same species, and cells with different transgenic alterations. Several biofilm-related characteristics impact electrogenic efficacy. Biofilm-related characteristics that impact electrogenic efficacy include, but are not limited to, the number of bacteria in the biofilm, the bacterial density in the biofilm, and the number of pili attached to the anode. In an embodiment a biofilm may be attached to, growing on, adhered to, coating, touching, covering or adjacent to the surface of an anode or anode chamber. The biofilm may improve survival of cells comprising the biofilm in adverse conditions including, but not limited to, non-preferred temperatures, pH ranges, heavy metal concentration and the like. Modulating the feedstock may modulate biofilm robustness.

Various substances may be added to the feedstock provided to a biofilm. Such substances may include additional organisms compatible with the transgenic microbe, mediator compounds, antibiotic compounds, additives for regulating or modulating an inducible promoter, and biofilm optimizers. Biofilm optimizers are compounds that modulate a metabolic property of at least one of the cells present in a biofilm, such a metabolic property may impact metabolism of available substrates or physiological cooperation between microbes within the biofilm or microbial fuel cell. Antibiotics that may be added to the feedstock are selected from the group of antibiotics to which the transgenic microbe is resistant.

Although improved biofilm formation and maintenance is desirable, it is recognized that over-production of the bacterial cell biofilm matrix may be detrimental to a microbial fuel system. For instance, overproduction of the bacterial cells may clog the microbial fuel cell, alter the environment of the microbial fuel cell, clog a filter between the anode and cathode chambers, increase the likelihood of bacterial cell death or yield a biofilm with a non-optimal thickness. Furthermore, cell division requires energy that could be transferred to the anode. Therefore, in an embodiment exogenous regulation of cell division (or cell replication) may occur. Such regulation may involve the use of inducible promoters.

By "heterologous nucleotide sequence" is intended a sequence that is not naturally occurring with the promoter sequence. While this nucleotide sequence is heterologous to the promoter sequence, it may be homologous, or native, or heterologous, or foreign, to the host cell. Heterologous nucleotide sequences of interest include, but are not limited to, nucleotide sequences of interest encoding substances that uncouple oxidation and phosphorylation. Uncoupling, interference or disruption of the normally coupled processes, oxidation and phosphorylation alters the proton gradient from the periplasmic space to the cytoplasm. For example in bacteria treated with an exogenous uncoupler such as dinitrophenol, the rate of substrate oxidation increases and electron flow to the anode may increase. Additional uncouplers include, but are not limited to, thermogenin, UCXP-1, UCP-2, and UCP-3, that would be expressed within the microbial cell. In an embodiment, a nucleic acid molecule having a nucleotide sequence encoding an uncoupling polypeptide such as, but not limited to, thermogenin, UCXP-1, UCP-2, and UCP-3 is operably linked to an inducible promoter. The bacterial cell may then be stably transformed with an expression cassette comprising an inducible promoter operably linked to an uncoupling nucleotide sequence of interest.

Anaerobic conditions may encompass both strict anaerobic conditions with no $O_2$ present and mild anaerobic conditions wherein the $O_2$ concentration occurs within a range from 0 to 15%, 0.001% to 12.5%, 0.001% to 10%, 0.001% to 7.5%, 0.001% to 5%, 0.01% to 4%, 0.01% to 3%, 0.01% to 2%, 0.01% to 1%, or 0.01% to 0.05%. Thus, bacteria in an anaerobic environment metabolize feedstock differently than in aerobic conditions. In certain embodiments aerobic conditions are desirable. In certain embodiments anaerobic conditions are desirable. *P. aeruginosa* rapidly utilizes oxygen, thus may generate anaerobic conditions. Anaerobic conditions may be established by utilizing an oxygen removing system. Oxygen removing enzyme systems include, but are not limited to, a glucose-glucose oxidase-catalase enzymatic $O_2$ removal system. Glucose oxidase converts glucose to uric acid and $H_2O_2$. Glucose oxidase is an oxygen dependent enzyme. The glucose oxidase and catalase reactions collectively halve the oxygen concentrations in each cycle. By "maintaining" anaerobic conditions around a biofilm is intended the establishment of anaerobic condition and sustaining said anaerobic conditions for a period of time including but not limited to, 30 seconds, 1 minute, 2 minutes, 5 minutes, 10 minutes, 15 minutes, 20 minutes, 25 minutes, 30 minutes, 45 minutes, 60 minutes, 2 hours, 3 hours, 4 hours, 5 hours, 6 hours, 7 hours, 10 hours, 15 hours, 20 hours, 24 hours, 36 hours, 48 hours, 60 hours, 72 hours, 84 hours, 96 hours, 108 hours, 5 days, 6 days, 7 days, 2 weeks, 3 weeks, 4 weeks, 1 month, 2 months, 3 months, 4 months, 5 months, 6 months, and 1 year. It is recognized that intermittent periods of aerobic conditions may occur particularly with regard to maintenance or introduction of feedstock to the microbial fuel cell, such as but not limited to, when sewage enters the fuel cell.

Methods of inoculating an anodic chamber include, but are not limited to, immersion of the anode in a culture, addition of bacteria to the anodic chamber, and addition of a matrix comprising a transgenic bacteria of the instant application.

In an embodiment, the microbial fuel cell, particularly the anodic compartment, is incubated with a 17 amino acid polypeptide from the C-terminus of the PilA peptide. The terminal 17 amino acids of the PilA protein mediates attachment to a variety of surfaces and reduces biofilm formation. In an embodiment the anodic chamber is pretreated or coated with the 17-mer, but the anode is not.

By anode is intended an electron acceptor. The anode may be of planar, cylindrical, layered spiral cylindrical, curved, angled or other geometrical shape such as but not limited to, a sheet, multiple sheets, wire mesh, porous tube, and sponge-like matrix. It is recognized that it is desirable for the anode to provide a large surface area to volume ratio. The anode may be removable from the microbial fuel cell. Optimal operation of the microbial fuel cell may involve cleaning or replacement of the anode. An anode may be constructed of any suitable material including but not limited to, metal (stainless steel), carbon, carbon nanotubes, carbon nanofibers, carbon cloth, carbon paper, platinum, graphite, graphite rods, graphite felts, graphite foams, graphite pellets, reticulated vitreous carbon (RVC) 97% porous, synthetic diamond, gold, aluminum, or other electrically conductive material. A porous metal, such as sintered steel, may provide a large surface area to volume ratio for the anode. For example, the anode may be a planar surface, multiple thin plates in close proximity with each other or a rolled planar surface or mesh. It is recognized that anode shape and anode material may be modified or optimized for different utilities of the microbial fuel cell. It is recognized that anodes may exhibit high surface area, low resistance, high conductivity, or a combination thereof and may allow high bacterial growth density. Nanomaterials are typically less than 1 micron in thickness.

An anode may be connected by a wire to the cathode. Suitable substances for the wire include, but are not limited to, copper or diamond.

The cathode of a microbial fuel cell may be an electrically conductive material including but not limited to, metal (stainless steel), carbon, carbon nanotubes, carbon nanofibers, carbon cloth, carbon paper, platinum, graphite, graphite rods, graphite felts, graphite foams, graphite pellets, reticulated vitreous carbon (RVC) 97% porous, synthetic diamond, silver, gold, aluminum, or other electrically conductive material.

A barrier such as a Nafion® membrane may separate the anodic and cationic chambers. The barrier slows, decreases, or prevents electrons from moving directly from the anode to the cathode; rather, the electrons flow through the wires of the electrical circuit. The barrier may be an ionomer membrane such as but not limited to a Nafion® perfluorosulfonic acid (PFSA) membrane (DuPont Fuel Cells, Inc). Excessive deposits of the biofilm on the barrier may impair function of the microbial fuel cell. Therefore it is advisable to maintain biofilm deposits on the barrier at a moderate level. Methods of regulating biofilm deposits include, but are not limited to, regulating bacterial cell division rates and precoating the barrier with a biofilm formation inhibitor. Biofilm formation inhibitors are known in the art and include the polypeptide having the amino acid sequence of the terminal 17 amino acids of the PilA protein, also known as the PilA 17mer. Alternatively the anode and cathode may be separable components as for instance an anodic tube that may be removable from the cathode portion of the microbial fuel cell.

Several microbial fuel cells could be electrically associated in series or parallel to create a battery of fuel cells. One or more of the microbial fuel cells could be disassembled and cleaned. It is recognized that one or more components of the microbial fuel cell may be cleaned. Such cleaning may involve chemical cleaning, mechanical cleaning, scavenging the biofilm utilizing species of *Bdellovibrio*, scavenging the biofilm utilizing a carnivorous organism such as but not limited to a fungi, or a combination thereof. *Bdellovibrio*, a bactivorous bacterium, feeds upon *P. aeruginosa* and temporarily reverses the polarity of the electrode to release bound pili.

A user of a microbial fuel cell may fabricate or obtain a microbial fuel cell. The user of the microbial fuel cell could then use electrodes proceeding from the anode and cathode to attach the fuel cell to a load. Thus, the user completes an electrical circuit from the anode through the load to the cathode. The user could, for example, by engaging a switch, cause electrical current created by the transgenic microbes to flow through the load. The transgenic microbes transfer electrons from the feedstock to the anode, the electrons proceed to flow through electrodes and the load to the cathode. A barrier blocks the electrons from flow through the interior of the fuel cell. Microbial fuel cells may be used in consumer electronics perhaps through a lithium/ion battery recharger or as a replacement for lithium/ion batteries. Microbial fuel cells may be used in electric plug-in automobiles or to recharge electric plug-in automobiles. Microbial fuel cells may generate power for residential and commercial buildings by tapping into organic wastes flushed from the buildings in the outgoing sewage pipes. Microbial fuel cells may be used for large waste treatment, farms, and utilities.

The microbial fuel cell electrical system may further include an ultracapacitor connected electrically in parallel in a paired system. Ultracapacitors have the advantageous ability to store power quickly and deliver it in relatively short bursts upon demand. Pairing an ultracapacitor with a fuel cell according to an embodiment of the invention enables a user of the paired system to have a continuous flow of power when beginning to start the system.

Furthermore, advantageous use can be made of the chemical reactions of the microbial fuel cell. For example, the products of the chemical reaction at the cathode may include free hydrogen gas when the microbial fuel cell is operated anaerobically. The hydrogen gas may be collected and utilized to power a classical hydrogen fuel cell. Also, microbial fuel cells emit very little carbon dioxide and may utilize carbon dioxide as a feedstock or remove it to biocarbonate by carbonic anhydrase as an attachment to the anode. The microbial fuel cell may be designed to emit usable sugars that can become an energy source for other devices. The microbial fuel cell may be operated aerobically to emit water as a byproduct. The water may be transferred to a water storage device or transferred to the external environment.

By "matrix" is intended a material in which something is embedded or enclosed. Matrices suitable for use in the current application include, but are not limited to, sponges, filters, beads, powders, tissues, granules, cassettes, cartridges and capsules.

The transgenic microbes of the instant application may be utilized in cleaning solutions and odor reduction systems.

The following examples are offered by way of illustration and not limitation.

EXPERIMENTAL

Example 1

Development of Static Biofilms on Simple Glass Surfaces in Feedstock

Circular glass coverslips were attached to the bottom of 35×10 mm polystyrene tissue culture dishes with small holes in the base (Falcon). The plates were exposed to UV irradiation overnight. (UV irradiation sterilizes the culture plates).

Bacterial cells were grown in Luria Bertani media (LB) overnight.

Aerobic LB, aerobic LBN (LB+1% $KNO_3$), or anaerobic LBN (3 ml) was placed in each tissue culture plate. The media was inoculated with $10^7$ cfu of bacterial cells. The plates were incubated at 37° C. for 24 hours. The media was removed and the plates were washed with saline buffer. LIVE/DEAD BacLight (Molecular Probes, Inc) bacterial viability stain (0.5 ml) was added to each plate. Images were acquired on a Zeiss LSM 510 laser scanning confocal unit attached to an Axiovert microscope with a 63×14 NA oil immersion objective. For two color images, samples were scanned sequentially at 488 nm and 546 nm. Syto 9 (green fluorescence) was detected through a 505-530 nm bandpass filter and propidium iodine (red fluorescence) was detected through a 560 nm longpass filter and presented in two channels of a 512×512 pixel, 8-bit image.

Example 2

Culture Media

LB media is 10 g/liter tryptone, 5 g/liter yeast extract, and 5 g/liter NaCl.

LBN media is 10 g/liter tryptone, 5 g/liter yeast extract, 5 g/liter NaCl and 10 g/liter $KNO_3$.

Example 3

Development of Biofilms in Circulated Feedstock

Bacteria are grown aerobically in LB at 37° C. until the stationary growth phase. Bacteria are diluted 1:50 into 1% trypticase soy broth. Flow cells are inoculated with 0.2 ml diluted bacteria. Flow cells and bacteria are incubated for 1 hour. After an hour, flow is initiated at a rate of 0.17 ml/min. The cells are incubated 3 days at room temperature. The cells are stained with a live/dead viability stain composed of SYTO 9 and propidium iodine (Molecular Probes, Inc.). Biofilm images are obtained using an LSM 510 confocal microscope (Carl Zeiss, Inc.). The excitation and emission wavelengths for green fluorescence are 488 nm and 500 nm, while those for red fluorescence are at 490 nm and 635 nm, respectively. All biofilm experiments are repeated at least 3 times. The live/dead ratios of the biofilms are calculated using the 3D for LSM (V.1.4.2) software (Carl Zeiss). Overall biofilm structure such as thickness, water channel, bacterial density (substrate coverage), roughness coefficient and total biomass in $m^3/m^2$ are assessed using COMSTAT software. COMSTAT analyzes stacks of images acquired with scanning confocal laser microscopy (SCLM) to quantify the 3-dimensional nature of biofilm structures. See Heydorn et al (2000) *Microbiology* 146 (Pt 10):2395, herein incorporated by reference in its entirety.

Example 4

Construction of *P. aeruginosa* Deletion Mutants

The *P. aeruginosa* strain PAO1 is used as the starting strain for construction of deletion mutations. Classical allelic replacement techniques are used to generate mutant strains. See Hoang et al (1998) *Gene* 212(1):77-86) An insertional mutagenesis cassette comprising a gentamicin resistant ($Gm^R$) nucleotide sequence, a green fluorescent protein (GFP) nucleotide sequence, and FLP recombinase target (FRT) sites flanking the gentamicin resistance sequence and the GFP sequence is developed for each gene of interest. After conjugal transfer or electroporation plasmid integrants are selected. The cells are grown in media containing 6% sucrose. The sucrose promotes deletion of the target sequence of interest. Mutants are confirmed via PCR or Southern blotting. Mutant cells undergo conjugal transfer with a cell containing a FLP-recombinase expressing plasmid such as pFLP2. pFLP2 contains the sacB sequence; growth on sucrose containing media cures the bacterial cells of the sacB containing plasmid. Expression of FLP recombinase allows excision of the FRT cassette. After curing of plasmid the *P. aeruginosa* deletion mutant strain is gentamicin sensitive. Multiple mutations such as double and triple mutants are constructed by similar methods.

Example 5

High-Throughput Microbial Fuel Cell Prototype

A small high-throughput microbial fuel cell (Pilus Cell) prototype was developed. A Millipore filtration apparatus of the type commonly used to collect cells on a 1 inch nitrocellulose filter was utilized to construct the Pilus Cell prototype. When used to collect cells on a filter for radioactivity measurements in a scintillation counter, a filter is placed on the sintered plastic surface of each well. The top portion of the apparatus is tightly screwed to the base portion. The top "cup" portion of the apparatus has rubber seals to prevent leakage from each well. The base portion includes a vacuum port. The Millipore filtration apparatus has 12 wells.

The filtration apparatus has been modified into a high-throughput device for screening and monitoring power generation by up to 12 different genetically engineered bacteria. Copper wires have been soldered to the base of twelve 2.54 cm×0.2 mm circular wafers of stainless steel. The milled steel was treated with acetone and then methanol to remove residual oils. The steel wafers were brushed with a wire brush to increase the surface area of the steel available for bacterial binding. The copper wire attached to the wafer represents the anode. The copper wires from each wafer were drawn through what was formerly the vacuum port of the apparatus. The copper wires were connected to a voltage/current measuring device. Each well may hold up to 15 mls of media; in these experiments 7 mls of media were used. Two holes were drilled into each of twelve grade 6 rubber stoppers that fit snugly in the wells. An 8 inch copper wire that extends 0.25 inches into the media in the anode was placed in the main hole of the stopper. This copper wire represents the cathode. This high-throughput device allows evaluation of up to 12 samples at a time. Once assembled, each well has the capacity to be an independent microbial fuel cell.

Example 6

High Through-Put Microbial Fuel Cell Voltage/Current Evaluation

The above described high-throughput microbial fuel cell prototype was used to evaluate voltage and current generation from wildtype *Pseudomonas aeruginosa* (POA), *Shewanella oneidensis*, and a mutant strain (pilT, bdlA, nirS, lasI, or fliC pilA). The entire high-throughput microbial fuel cell prototype was assembled and secured by a bolt on the top of the apparatus. Each well utilized in the experiment was sterilized by treatment with ethanol. The ethanol was removed and the apparatus was dried in a germ-free laminar flow hood. LB+1% $KNO_3$ media (7 ml) was placed in each well utilized in the experiment. A stationary phase grown aerobic culture (70 µl, a 1:100 dilution) for each bacterial sample (wildtype *Pseudomonas*, *Shewenella*, and a mutant strain) was added to the media in the well. A medium alone control well was also prepared and monitored. Rubber stoppers and copper cathode wires were treated with ethanol prior to securing the stoppers in the wells. The device was incubated at 37° C. for 24 hours under anaerobic conditions.

Measurements were recorded as described elsewhere herein. The stoppers were removed and the media was aspirated away. Saline (0.9%) was gently applied to each well. The saline solution was removed by aspiration. The saline wash was performed three times. Ethanol was swabbed over the plastic regions of each well. LB+1% $KNO_3$ media (7 ml) was added to each well. The recording process was repeated. Results from one such experiment are presented in FIG. 1.

Example 7

Voltage and Current Monitoring of the High-throughput Microbial Fuel Cell Prototype Measurements were obtained using a LabJack U12, 8 channel 12 bit USB ND for data acquisition system. Four channels were used to monitor microbial fuel cell voltages. The 3 cm copper anodes were connected to four LT1012 high input impendence buffer amplifiers. The outputs of these amplifiers were then connected to the channel AIO-AI3 inputs of the Labjack A/D. Current measurements were made by connecting a LT1101 instrumentation amplifier across the 1K current sense resistor. By measuring the voltage drop across the resistor and utilizing Ohm's law ($I=E/R$) the current flowing in the cell circuit can be calculated.

The measurement system utilized allows voltage and current measurements to be done remotely via the Internet. The system utilizes eight different graphic monitoring systems that can be configured to monitor various combinations of voltages and currents as dictated by the experimental design.

Example 8

Development of Microbial Fuel Cell with Increased Anode Surface Area

A 23-plate stainless steel 314 anode system is constructed. The first 21 plates are of the following dimensions: 0.05× 9.851×7.554 inches. This involves a total surface area of 197.56 inches. The other two plates are 0.05×9.851×7.884 inches. The two larger plates serve as "legs" facing either in or toward the Nafion membrane and adding an additional 96.2 inches of surface area. Thus the total estimated surface area is approximately 294 inches. The two larger plates provide support to the 21 plate component. The electrode from the anode to the cathode compartment is stainless steel and fitted with Swagelok fittings into similar fittings embedded within the cathode.

A single plate of hot, isostatic pressed graphite (GraphiteStore.com) of 0.125×9.6×4.65 inches is used for the cathode.

After the anode is assembled, the anode is treated with 1% bleach, then 95% ethanol, and then 70% ethanol. Small 1×1× 0.05 inch stainless steel wafers are used to monitor biofilm formation. The anode is incubated in a Coy anaerobic chamber in 1 liter of LB+1% $KNO_3$ at 37° C. for 24 hours inoculated with bacteria.

Experiments are performed with wild-type bacteria or with various mutants. The overall efficiency of the wild-type and mutant strains is compared. The complete anode assembly with a mature biofilm attached is submerged in anaerobic 0.9% NaCl solution and removed from the solution. Submersion and removal may be repeated. (Unattached bacteria are removed by this process.) The anode with the attached mature biofilm is placed in the large microbial fuel cell assembly. Two plastic boxes, one containing the anode, the other the cathode are filled with LB+1% $KNO_3$. The anodic and cathodic chambers are treated with glucose oxidase. Glucose oxidase converts glucose to uric acid and $H_2O_2$. $H_2O_2$ is treated with catalase. The glucose oxidase and catalase reactions lower the oxygen concentration. The anode is poised at approximately 250-400 mV (versus Ag/AgCl). A Clark-type or World Precision Instrument $O_2$ electrode is attached to both the anode and cathode sections. Flow of fresh anaerobic media through the anodic compartment is accomplished using peristaltic pumps at a flow rate of 0.05 ml/min.

Similar experiments are performed with wild-type, single, double, triple quadruple, quintuple, and multiple mutant strains. Current and voltage output are monitored using a LabJack system as described above herein or an Agilent 34970-A data acquisition system that is linked to electronic databases. This system allows monitoring of current in the micro-ampere range and voltage in the micro to millivolt range.

Example 9

P. aeruginosa Mutant Strains

The PAO1 strain was used to prepare mutant strains. pilT, bdlA, nirS, and lasI single disruption mutations were constructed. pilT bdlA, bdlA nirS, bdlA lasI, nirS pilT, nirS lasI, and lasI pilT double disruption mutant strains were constructed. pilT bdlA nirS, bdlA lasI pilT, nirS lasI bdlA triple disruption mutant strains were constructed. A pilT bdlA nirS lasI quadruple disruption mutant strain was constructed.

A PAO1 strain stably comprising araBAD-ftsZ was constructed. The PAO1 araBAD-ftsZ strain was used to prepare mutant strains. pilT, bdlA, nirS, and lasI single disruption mutations were constructed in the PAO1 araBAD-ftsZ background. pilT bdlA, bdlA nirS, bdlA lasI, nirS pilT, nirS lasI, and lasI pilT double disruption mutations were constructed in the PAO1 araBAD-ftsZ background. pilT bdlA nirS, bdlA lasI pilT, and nirS lasI bdlA triple disruption mutations were constructed in the PAO1 araBAD-ftsZ background. A pilT bdlA nirS lasI quadruple disruption mutant strain was constructed in the PAO1 araBAD-ftsZ background.

A PAO1 strain stably comprising araBAD-ftsZ and a siRNA construct (PA0730) was constructed. The PAO1 araBAD-ftsZ PA0730 strain was used to prepare mutant strains. pilT, bdlA, nirS, and lasI single disruption mutations were constructed in the PAO1 araBAD-ftsZ PA0730 background. pilT bdlA, bdlA nirS, bdlA lasI, nirS pilT, nirS lasI, and lasI pilT double disruption mutations were constructed in the PAO1 araBAD-ftsZ PA0730 background. pilT bdlA nirS, bdlA lasI pilT, and nirS lasI bdlA triple disruption mutations were constructed in the PAO1 araBAD-ftsZ PA0730 background. A pilT bdlA nirS lasI quadruple disruption mutant strain was constructed in the PAO1 araBAD-ftsZ PA0730 background.

All publications, patents, and patent applications mentioned in the specification are indicative of the level of those skilled in the art to which this invention pertains. All publications, patents, and patent applications are herein incorporated by reference to the same extent as if each individual publication or patent application was specifically and individually incorporated by reference.

With respect to the use of substantially any plural and/or singular terms herein, those having skill in the art may translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claims, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

Having described the invention with reference to the exemplary embodiments, it is to be understood that it is not intended that any limitations or elements describing the exemplary embodiment set forth herein are to be incorporated into the meanings of the patent claims unless such limitations or elements are explicitly listed in the claims. Likewise, it is to be understood that it is not necessary to meet any or all of the identified advantages or objects of the invention disclosed herein in order to fall within the scope of any claims, since the invention is defined by the claims and since inherent and/or unforeseen advantages of the present invention may exist even though they may not be explicitly discussed herein.

Although the foregoing invention has been described in some detail by way of illustration and example for purposes of clarity of understanding, it will be obvious that certain changes and modifications may be practiced within the scope of the appended claims.

That which is claimed:

1. A transgenic *Pseudomonas aeruginosa* cell stably transformed with an isolated nucleic acid molecule that disrupts an endogenous nucleotide sequence of interest selected from the group comprising pilT (SEQ ID NO:1), pilA (SEQ ID NO:2), nirS (SEQ ID NO:3), bdlA (SEQ ID NO:4), lasI (SEQ ID NO:5), lasR (SEQ ID NO:6), ftsZ (SEQ ID NO:7), and fliC (SEQ ID NO:8) wherein said microbial cell exhibits decreased expression of said endogenous nucleotide sequence of interest and said cell exhibits an altered electrogenic efficacy.

2. The transgenic cell of claim 1, wherein at least 2 endogenous nucleotide sequences of interest are disrupted and wherein said disrupted endogenous nucleotide sequences are selected from the group comprising pilT (SEQ ID NO:1), pilA (SEQ ID NO:2), nirS (SEQ ID NO:3), bdlA (SEQ ID NO:4), lasI (SEQ ID NO:5), lasR (SEQ ID NO:6), ftsZ (SEQ ID NO:7), and fliC (SEQ ID NO:8).

3. The transgenic cell of claim 2, wherein said at least two disrupted endogenous nucleotide sequences are selected from the group of double nucleotide sequences of interest comprising pilT (SEQ ID NO:1) bdlA (SEQ ID NO:4); bdlA (SEQ ID NO:4) nirS (SEQ ID NO:3); bdlA (SEQ ID NO:4) lasI (SEQ ID NO:5); nirS (SEQ ID NO:3) pilT (SEQ ID NO:1); nirS (SEQ ID NO:3) lasI (SEQ ID NO:5); lasI (SEQ ID NO:5) pilT (SEQ ID NO:1); ftsZ (SEQ ID NO:7) pilT (SEQ ID NO:1); ftsZ (SEQ ID NO:7) bdlA (SEQ ID NO:4); ftsZ (SEQ ID NO:7) nirS (SEQ ID NO:3); and ftsZ (SEQ ID NO:7) lasI (SEQ ID NO:5).

4. The transgenic cell of claim 1, wherein said cell has a reduced proliferative capability as compared to a non-transgenic cell.

5. The transgenic cell of claim 1, wherein said cell has a reduced virulence as compared to a non-transgenic cell.

6. The transgenic cell of claim 5 wherein said reduced virulence is in mammals or plants.

7. The transgenic cell of claim 1, wherein said cell exhibits reduced motility as compared to a non-transgenic cell.

8. The transgenic cell of claim 1, wherein said cell exhibits altered pilus sticking as compared to a non-transgenic cell.

9. The transgenic cell of claim 1, wherein said cell exhibits altered twitching motility as compared to a non-transgenic cell.

10. The transgenic bacterial cell of claim 1 wherein said cell exhibits an increased current output/bacterial cell when said bacterial cell is a component of a microbial fuel cell.

11. The transgenic cell of claim 1, wherein said cell exhibits increased electron transfer to an anode.

12. The transgenic cell of claim 11, wherein said electron transfer is direct or indirect.

13. A matrix comprising a transgenic cell of claim 1.

14. The matrix of claim 13 wherein said matrix is selected from the group comprising sponges, filters, beads, powders, tissues, cassettes, cartridges, and capsules.

* * * * *

SEQUENCE LISTING

```
<160> NUMBER OF SEQ ID NOS: 8

<210> SEQ ID NO 1
<211> LENGTH: 1035
<212> TYPE: DNA
<213> ORGANISM: Pseudomonas aeruginosa

<400> SEQUENCE: 1
atggatatta ccgagctgct cgccttcagt gccaaacagg gcgcttcgga cctgcacctc      60
tccgccggcc tgccacccat gatccgggtg gatggcgatg tacgccggat caacctgcca     120
ccgctggaac acaagcaggt gcatgcgctg atctacgaca tcatgaacga caagcagcgc     180
aaggacttcg aggaattcct cgagaccgac ttctccttcg aggtgccggg cgtcgcgcgt     240
ttccgggtca acgccttcaa ccagaaccgt ggcgccggcg cggtattccg gaccattccc     300
tccaaggtac tgaccatgga ggagcttggc atgggagaag tgttcaaacg tgtttcagac     360
gtcccgcgcg ggttggtact ggtcaccggg ccgaccggtt cgggcaagtc caccaccctg     420
gcggcgatgc tcgattacct gaacaacacc aagtaccacc acatcctcac catcgaggac     480
ccgatcgaat tcgtccacga atcgaagaag tgcctggtca accagcgcga ggtgcatcgc     540
gacaccctcg gcttcagcga agcgctgcgc tcggcgctgc gggaggaccc ggacatcatc     600
ctggtcggcg agatgcgcga cctggaaacc atccgcctgg ccctgaccgc ggcggagacc     660
ggccacctgg tattcggcac cctgcacacc acctcggcgg cgaagaccat cgaccgggtg     720
gtcgacgtgt tcccggccga ggaaaaggcc atggttcgct cgatgctctc cgagtcgctg     780
caatcggtga tctcgcagac cctgatcaag aagatcggcg gcggccgggt ggcggcccac     840
gagatcatga tcggcacccc ggcgatccgc aacctgatcc gcgaggacaa ggtcgcgcag     900
atgtattcgg cgatccagac cggcggctcg ctgggcatgc agaccctcga catgtgcctc     960
aagggcctgg tcgccaaggg cctgatcagc cgcgagaacg cccgcgagaa ggcgaagatc    1020
ccggaaaact tctga                                                    1035

<210> SEQ ID NO 2
<211> LENGTH: 450
<212> TYPE: DNA
<213> ORGANISM: Pseudomonas aeruginosa

<400> SEQUENCE: 2
atgaaagctc aaaaaggctt taccttgatc gaactgatga tcgtggttgc gatcatcggt      60
atcctggcgg caattgccat tccccagtat cagaactatg ttgcgcgttc ggaaggtgct     120
tcggcgctgg cgacgatcaa cccgctgaag accactgttg aagagtcgct gtcgcgtgga     180
attgctggta gcaaaattaa aattggtact actgcttcta ctgcgaccga acatatgtc     240 ggcgtcgagc cggatgccaa caagttgggt gtaattgctg tagcaatcga agatagtggt     300
gcgggtgata ttacctttac cttccagact ggtacctcta gtcccaagaa tgctactaaa     360
```

```
gttatcactc tgaaccgtac tgcggatggg gtctgggctt gtaaatctac ccaggatccg     420
atgttcactc cgaaaggttg tgataactaa                                     450
```

<210> SEQ ID NO 3
<211> LENGTH: 1707
<212> TYPE: DNA
<213> ORGANISM: Pseudomonas aeruginosa

<400> SEQUENCE: 3

```
atgccatttg gcaagccact ggtgggcacc ttgctcgcct cgctgacgct gctgggcctg      60
gccaccgctc acgccaagga cgacatgaaa gccgccgagc aataccaggg tgccgcttcc     120
gccgtcgatc ccgctcacgt ggtgcgcacc aacggtgccc ccgacatgag tgaaagcgag     180
ttcaacgagg ccaagcagat ctacttccaa cgctgcgccg gttgccacgg cgtcctgcgc     240
aagggcgcca ccggcaagcc gctgaccccg acatcaccc agcaacgcgg ccagcaatac      300
ctggaagcgc tgatcaccta cggcaccccg ctgggcatgc cgaactgggg cagctccggc     360
gagctgagca aggaacagat caccctgatg gccaagtaca tccagcacac cccgccgcaa     420
ccgccggagt ggggcatgcc ggagatgcgc gaatcgtgga aggtgctggt gaagccggag     480
gaccggccga agaaacagct caacgacctc gacctgccca acctgttctc ggtgaccctg     540
cgcgacgccg gcagatcgc cctggtcgac ggcgacagca agaagatcgt caaggtcatc     600
gataccggct atgccgtgca tatctcgcgg atgtccgctt ccggccgcta cctgctggtg     660
atcggccgcg acgcgcggat cgacatgatc gacctgtggg ccaaggagcc gaccaaggtc     720
gccgagatca agatcggcat cgaggcgcgc tcggtggaaa gctccaagtt caagggctac     780
gaggaccgct acaccatcgc cggcgcctac tggccgccgc agttcgcgat catggacggc     840
gagaccctgg aaccgaagca gatcgtctcc acccgcggca tgaccgtaga cacccagacc     900
taccaccagg aaccgcgcgt ggcggcgatc atcgcctccc acgagcaccc cgagttcatc     960
gtcaacgtga aggagaccgg caaggtcctg ctggtcaact acaaggatat cgacaacctc    1020
accgtcacca gcatcggtgc ggcgccgttc ctccacgacg gcggctggga cagcagccac    1080
cgctacttca tgaccgccgc caacaactcc aacaaggttg ccgtgatcga ctccaaggac    1140
cgtcgcctgt cggccctggt cgacgtcggc aagacccccgc accggggcg tggcgccaac    1200 ttcgtgcatc ccaagtacgg cccggtgtgg agcaccagcc acctgggcga cggcagcatc    1260
tcgctgatcg gcaccgatcc gaagaaccat ccgcagtacg cctggaagaa agtcgccgaa    1320
ctacagggcc agggcggcgg ctcgctgttc atcaagaccc atccgaagtc ctcgcacctc    1380
tacgtcgaca ccaccttcaa ccccgacgcc aggatcagcc agagcgtcgc ggtgttcgac    1440
ctgaagaacc tcgacgccaa gtaccaggtg ctgccgatcg ccgaatgggc cgatctcggc    1500
gaaggcgcca agcgggtggt gcagcccgag tacaacaagc gcggcgatga agtctggttc    1560
tcggtgtgga acggcaagaa cgacagctcc gcgctggtgg tggtgacga caagaccctg    1620 aagctcaagg ccgtggtcaa ggacccgcgg ctgatcaccc cgaccggtaa gttcaacgtc    1680
tacaacaccc agcacgacgt gtactga                                       1707
```

<210> SEQ ID NO 4
<211> LENGTH: 1254
<212> TYPE: DNA
<213> ORGANISM: Pseudomonas aeruginosa

<400> SEQUENCE: 4

```
atggcggccc tggaccgctc catggcgcgc gtggagttcg atccggacgg caatatcacc      60
```

```
gatgccaatg agaatttcct gaccctgctg ggctaccgcc gcgacgagat cctcggcaaa    120
ccgcatcgcc agctttgcga cggcgcctac gcgcaatcgg aagactaccg gcgcttctgg    180
gaacgcctgc ggcgcggcga acactttttcc ggccgctgca agcgcattac ccgcgagggc    240
cggccactct ggctggaagc cacctacaac cccgtacgcg acgggcaggg tcgactgctc    300
aaggtggtca gtacgccag cgacatcgat gccatcgtcc accaggaaca cgagatgcag    360
agcaagctgg atgccctgtc ccgctcgatg gcgatgatcg agttcgacct cgacggcaat    420
gtcctcgcgg ccaacgacaa cttcctcgcc accatgggct atggccgggc cgagctggcc    480
agcgccaacc accgtcagtt ctgcgaaccg ggctaccgcg acggcccaca gtacgccgac    540
ctctggcgcc gcctgaaccg cggcgagtac gtcaccgggc agttccgccg ggtccaccgc    600 aacgccagc cggtctggct ggaagccagc tacaacccgg tctacgacgc cgacggcaag    660
ctctacaagg tggtcaagtt cgccagcgat gtcagcgacc gcatgcgccg ctaccaggcc    720
gaggcggaca cgcccacca ggcccatacc ctgtccaccg agacccgcac ggtcgccgaa    780
cacggcgcgc tgatcatcca gagcgcggtg gaggaaatgc tcaagatcgc gaataccctg    840
gatgcttcct cgctgaacat cggcgaactg tcacagcact cgcaacagat cacctcgatc    900
gtcaacacca tccgcgagat cgccgagcag accaacctgc tcgccctcaa tgccgccatc    960
gaggccgccc gcgccggcga ccagggtcgc ggcttcgccg tggtggccga cgaggtgcgg   1020
caactggcgg aacgcaccag caagtcgacc aaggagatcg ccgacatgat cggtcgcatc   1080
cagaccggca cccgcagcgt catcgacgac atgcagcaca gccaggaaca ggcgcggcgc   1140
ggcgtggagc tggccaacga ggccggcgcg gcgatccttg gcatccgcga gagcacgcac   1200
aaggtggtag aagcggtgca gcagttctcg cgcacccctca acgccgatct ctag         1254

<210> SEQ ID NO 5
<211> LENGTH: 606
<212> TYPE: DNA
<213> ORGANISM: Pseudomonas aeruginosa

<400> SEQUENCE: 5
atgatcgtac aaattggtcg gcgcgaagag ttcgataaaa aactgctggg cgagatgcac      60
aagttgcgtg ctcaagtgtt caaggagcgc aaaggctggg acgttagtgt catcgacgag    120
atggaaatcg atggttatga cgcactcagt cctattacca tgttgatcca ggaagatact    180
cctgaagccc aggttttcgg ttgctggcga attctcgata ccactggccc ctacatgctg    240
aagaacacct tcccggagct tctgcacggc aaggaagcgc cttgctcgcc gcacatctgg    300
gaactcagcc gtttcgccat caactctgga cagaaaggct cgctgggctt ttccgactgt    360
acgctggagg cgatgcgcgc gctggcccgc tacagcctgc agaacgacat ccagacgctg    420
gtgacggtaa ccaccgtagg cgtggagaag atgatgatcc gtgccggcct ggacgtatcg    480
cgcttcggtc cgcacctgaa gatcggcatc gagcgcgcgg tggccttgcg catcgaactc    540
aatgccaaga cccagatcgc gctttacggg ggagtgctgg tggaacagcg actggcggtt    600
tcatga                                                               606

<210> SEQ ID NO 6
<211> LENGTH: 720
<212> TYPE: DNA
<213> ORGANISM: Pseudomonas aeruginosa

<400> SEQUENCE: 6
atggccttgg ttgacggttt tcttgagctg gaacgctcaa gtggaaaatt ggagtggagc      60
```

```
gccatcctgc agaagatggc gagcgacctt ggattctcga agatcctgtt cggcctgttg    120
cctaaggaca gccaggacta cgagaacgcc ttcatcgtcg caactaccc ggccgcctgg    180 cgcgagcatt acgaccgggc tggctacgcg cgggtcgacc cgacggtcag tcactgtacc   240
cagagcgtac tgccgatttt ctgggaaccg tccatctacc agacgcgaaa gcagcacgag   300
ttcttcgagg aagcctcggc cgccggcctg gtgtatgggc tgaccatgcc gctgcatggt   360
gctcgcggcg aactcggcgc gctgagcctc agcgtggaag cggaaaaccg ggccgaggcc   420
aaccgtttca tggagtcggt cctgccgacc ctgtggatgc tcaaggacta cgcactgcag   480
agcggtgccg gactggcctt cgaacatccg gtcagcaaac cggtggttct gaccagccgg   540
gagaaggaag tgttgcagtg gtgcgccatc ggcaagacca gttgggagat atcggttatc   600
tgcaactgct cggaagccaa tgtgaacttc catatgggaa atattcggcg aagttcggt    660 gtgacctccc gccgcgtagc ggccattatg gccgttaatt tgggtcttat tactctctga   720
```

<210> SEQ ID NO 7
<211> LENGTH: 1185
<212> TYPE: DNA
<213> ORGANISM: Pseudomonas aeruginosa

<400> SEQUENCE: 7

```
atgtttgaac tggtcgataa catcgcacaa accgccgtca taaaagtgat cggtgtaggt    60
ggtggtggcg gcaacgccgt caatcacatg gccaagaaca acgtcgaggg cgtcgagttc   120
atctgcgcca acaccgacgc acaagcgctg aagaacatcg cggcgcgcac cgttctgcaa   180
ctcggcccgg gcgtcaccaa ggggctgggt gccggcgcca atccggaagt cggtcgtcag   240
gcggctctgg aagatcgcga gcgcattttcc gaagtgctgg aaggcgccga catggtcttc   300
atcaccaccg gcatgggtgg cggcaccggt accgcgccc gccgatcat cgccgaagtg   360 gcgaaggaaa tgggcatcct caccgtcgcg gtggtgaccc gccgttccc gttcgaaggt   420 cgcaagcgca tgcagatcgc cgacgagggc atccgcgcgc tggccgagag cgtcgattcg   480
ctgatcacca tcccgaacga gaagctgctg accatcctcg gcaaggacgc cagcctgctg   540
gccgccttcg ccaaggccga tgacgtgctg ccggtgccg tgcgcggtat ctccgacatc   600
atcaagcgtc cgggcatgat caacgtcgac ttcgccgacg tgaagaccgt catgagcgaa   660
atgggcatgg cgatgatggg taccggctgc gccagcggtc cgaaccgtgc ccgcgaggcc   720
accgaggcgg caatccgcaa cccgctgctg gaagacgtca acctgcaggg cgcgcgcggc   780
atcctggtga acatcaccgc gggtccggac ctgtccctgg gcgagtactc cgatgtcggc   840
aacatcatcg aacagttcgc ttccgagcac gccactgtga aggtgggcac cgtgatcgac   900
gcggacatgc gcgatgagct gcacgtcacc gtagtcgcca ccggcctggg cgcgcgcctg   960
gagaaaccgg tgaaggtcgt cgacaacacc gtgcagggca gtgcagccca ggcagccgct  1020
ccggcccagc gcgagcagca gtcggtgaac taccgcgacc tcgaccgtcc taccgtgatg  1080
cgcaaccagt ctcacggcag cgcggcgacc gcggccaagc tgaacccgca ggatgacctg  1140
gattacctgg atatcccggc gttcctgcgt cgtcaggccg attga                  1185
```

<210> SEQ ID NO 8
<211> LENGTH: 1467
<212> TYPE: DNA
<213> ORGANISM: Pseudomonas aeruginosa

<400> SEQUENCE: 8

```
atggcccttta cagtcaacac gaacattgct tccctgaaca ctcagcgcaa cctgaatgct    60
```

```
tcttccaacg acctcaacac ctcgttgcag cgtctgacca ccggctaccg catcaacagt    120
gccaaggacg atgctgccgg cctgcagatc tccaaccgcc tgtccaacca gatcagcggt    180
ctgaacgttg ccacccgcaa cgccaacgac ggcatctccc tggcgcagac cgctgaaggt    240
gccctgcagc agtccaccaa tatcctgcag cgtatccgcg acctggccct gcaatccgcc    300
aacggctcca acagcgacgc cgaccgtgcc gccctgcaga agaagtcgc tgcgcaacag     360 gccgaactga cccgtatctc cgataccacc accttcggtg gccgcaagct gctcgacggc    420
tccttcggca ccaccagctt ccaggtcggt tccaacgcct acgagaccat tgacatcagc    480
ctgcagaatg cctctgccag cgccatcggt tcttaccagg tcggcagcaa cggcgcgggt    540
accgtcgcca gcgtagcggg caccgcgacc gcttcgggca tcgcctcggg caccgtcaac    600
ctggtcggtg gcggtcaggt gaagaacatc gccatcgccg ccggcgatag cgccaaggcc    660
atcgccgaga agatggacgg tgcgatcccg aacctgtcgg ctcgtgcccg taccgtgttc    720
accgctgatg tcagcggcgt gaccggtggt tcgctgaact tcgacgtaac cgttggcagc    780
aacaccgtga gcctggcagg cgtgacctcc actcaggatc tggccgacca actgaactcc    840
aactcgtcga agctgggcat cactgccagc atcaacgaca agggtgtact gaccatcacc    900
tccgctaccg gcgagaacgt caagttcggt gcgcagaccg gtaccgctac tgccggtcag    960
gtcgcagtga aggtccaggg ttccgacggc aagttcgaag cggccgccaa gaacgtggta   1020
gctgccggta ctgccgctac caccaccatc gtgaccggct acgtgcaact gaactcgccg   1080
accgcctact cggtcagcgg taccggcacc caggcttcgc aggtcttcgg caacgccagc   1140
gccgcgcaga agagcagcgt tgccagcgtc gacatctcca ctgccgacgg cgcccagaac   1200
gccatcgcgg tagtcgataa cgccctggct gcgatcgacg cccagcgtgc tgacctcggt   1260
gctgttcaga accgcttcaa gaacactatc gacaacctga ccaacatctc ggaaaacgct   1320
accaacgctc gtagccgcat caaggacacc gacttcgctg ccgaaaccgc ggcgctgtcg   1380
aagaaccagg tgctgcaaca ggccggtacc gcgatcctgg cccaggccaa ccagctgccg   1440
caggcggtcc tgagcctgct gcgctaa                                      1467
```